(12) United States Patent
Finch

(10) Patent No.: US 10,675,450 B2
(45) Date of Patent: Jun. 9, 2020

(54) DEVICES AND METHODS FOR TREATING HEART FAILURE

(71) Applicant: CORVIA MEDICAL, INC., Tewksbury, MA (US)

(72) Inventor: Matthew J. Finch, Medford, MA (US)

(73) Assignee: Corvia Medical, Inc., Tewksbury, MA (US)

( * ) Notice: Subject to any disclaimer, the term of this patent is extended or adjusted under 35 U.S.C. 154(b) by 0 days.

(21) Appl. No.: 14/645,416

(22) Filed: Mar. 11, 2015

(65) Prior Publication Data

US 2017/0113026 A1 Apr. 27, 2017

Related U.S. Application Data

(60) Provisional application No. 61/952,113, filed on Mar. 12, 2014.

(51) Int. Cl.
*A61M 27/00* (2006.01)

(52) U.S. Cl.
CPC .................................. *A61M 27/002* (2013.01)

(58) Field of Classification Search
CPC .. A61F 5/0076; A61F 2/04; A61F 2/24; A61F 2/90; A61F 2/82; A61M 27/002
See application file for complete search history.

(56) References Cited

U.S. PATENT DOCUMENTS

| | | |
|---|---|---|
| 3,837,345 A | 9/1974 | Matar |
| 3,874,388 A | 4/1975 | King et al. |
| 4,018,228 A | 4/1977 | Goosen |
| 4,373,216 A | 2/1983 | Klawitter |
| 4,491,986 A | 1/1985 | Gabbay |
| 4,655,217 A | 4/1987 | Reed |
| 4,705,507 A | 11/1987 | Boyles |
| 5,100,423 A | 3/1992 | Fearnot |

(Continued)

FOREIGN PATENT DOCUMENTS

| | | |
|---|---|---|
| CN | 1218379 A | 6/1999 |
| CN | 1556719 A | 12/2004 |

(Continued)

OTHER PUBLICATIONS

Ad et al.; A one way valved atrial septal patch: A new surgical technique and its clinical application; The Journal of Thoracic and Cardiovascular Surgery; 111; pp. 841-848; Apr. 1996.

(Continued)

*Primary Examiner* — Ariana Zimbouski
(74) *Attorney, Agent, or Firm* — Shay Glenn LLP

(57) ABSTRACT

The present teachings provide a device and methods of making and using thereof. Specifically, one aspect of the present teachings provides a self-expandable device with a braided structure comprising a shunt, a distal retention flange, and a proximal retention flange. Upon the device being deployed at a treatment location, the distal retention flange or the proximal retention flange transitions to have a diameter that is greater than the diameter of the shunt portion. And the shunt portion has a braid angle θ. Another aspect of the present teachings provide that the ratio of flange/shunt diameter equals or greater than 1/sin θ. Yet another aspect of the present teachings provides an axial constraining mechanism to reinforce the shunt portion.

19 Claims, 16 Drawing Sheets

(56) References Cited

U.S. PATENT DOCUMENTS

| | | |
|---|---|---|
| 5,108,420 A | 4/1992 | Marks |
| 5,171,233 A | 12/1992 | Amplatz et al. |
| 5,284,488 A | 2/1994 | Sideris |
| 5,332,402 A | 7/1994 | Teitelbaum |
| 5,334,217 A | 8/1994 | Das |
| 5,387,219 A | 2/1995 | Rapper |
| 5,413,599 A | 5/1995 | Imachi et al. |
| 5,429,144 A | 7/1995 | Wilk |
| 5,433,727 A | 7/1995 | Sideris |
| 5,464,449 A | 11/1995 | Ryan et al. |
| 5,478,353 A | 12/1995 | Yoon |
| 5,488,958 A | 2/1996 | Topel et al. |
| 5,556,386 A | 9/1996 | Todd |
| 5,556,408 A | 9/1996 | Farhat |
| 5,693,090 A | 12/1997 | Unsworth et al. |
| 5,702,412 A | 12/1997 | Popov et al. |
| 5,725,552 A | 3/1998 | Kotula et al. |
| 5,741,297 A | 4/1998 | Simon |
| 5,824,071 A | 10/1998 | Nelson et al. |
| 5,846,261 A | 12/1998 | Kotula et al. |
| 5,876,436 A | 3/1999 | Vanney et al. |
| 5,893,369 A | 4/1999 | Lemole |
| 5,944,738 A | 8/1999 | Amplatz et al. |
| 5,964,754 A | 10/1999 | Osypka |
| 6,050,936 A | 4/2000 | Schweich et al. |
| 6,059,827 A | 5/2000 | Fenton |
| 6,068,635 A | 5/2000 | Gianotti |
| 6,120,534 A | 9/2000 | Ruiz |
| 6,123,682 A | 9/2000 | Knudson et al. |
| 6,123,715 A | 9/2000 | Amplatz |
| 6,152,937 A | 11/2000 | Peterson et al. |
| 6,156,055 A | 12/2000 | Ravenscroft |
| 6,168,622 B1 | 1/2001 | Mazzocchi |
| 6,190,353 B1 | 2/2001 | Makower et al. |
| 6,193,734 B1 | 2/2001 | Bolduc et al. |
| 6,210,338 B1 | 4/2001 | Afremov et al. |
| 6,214,029 B1 | 4/2001 | Thill et al. |
| 6,241,678 B1 | 6/2001 | Afremov et al. |
| 6,258,119 B1 | 7/2001 | Hussein et al. |
| 6,283,983 B1 | 9/2001 | Makower et al. |
| 6,286,512 B1 | 9/2001 | Loeb et al. |
| 6,334,864 B1 | 1/2002 | Amplatz et al. |
| 6,350,277 B1 | 2/2002 | Kocur |
| 6,355,052 B1 | 3/2002 | Neuss et al. |
| 6,355,056 B1 | 3/2002 | Pinheiro |
| 6,357,735 B2 | 3/2002 | Haverinen |
| 6,383,195 B1 | 5/2002 | Richard |
| 6,391,036 B1 | 5/2002 | Berg et al. |
| 6,395,017 B1 | 5/2002 | Dwyer et al. |
| 6,402,777 B1 | 6/2002 | Globerman et al. |
| 6,409,716 B1 | 6/2002 | Sahatjian et al. |
| 6,440,152 B1 | 8/2002 | Gainor et al. |
| 6,454,795 B1 | 9/2002 | Chuter |
| 6,458,153 B1 | 10/2002 | Bailey et al. |
| 6,468,301 B1 | 10/2002 | Amplatz et al. |
| 6,468,303 B1 * | 10/2002 | Amplatz ............... A61B 17/11 623/1.2 |
| 6,527,746 B1 | 3/2003 | Oslund et al. |
| 6,572,652 B2 | 6/2003 | Shaknovich |
| 6,579,311 B1 | 6/2003 | Makower |
| 6,599,308 B2 | 7/2003 | Amplatz |
| 6,626,936 B2 | 9/2003 | Stinson |
| 6,638,257 B2 | 10/2003 | Amplatz |
| 6,645,143 B2 | 11/2003 | Vantassel et al. |
| 6,666,885 B2 | 12/2003 | Moe |
| 6,699,256 B1 | 3/2004 | Logan et al. |
| 6,712,836 B1 | 3/2004 | Berg et al. |
| 6,719,768 B1 | 4/2004 | Cole et al. |
| 6,719,934 B2 * | 4/2004 | Stinson ............... A61F 2/90 264/103 |
| 6,837,901 B2 | 1/2005 | Rabkin et al. |
| 6,866,679 B2 | 3/2005 | Kusleika |
| 6,911,037 B2 | 6/2005 | Gainor et al. |
| 6,913,614 B2 | 7/2005 | Marino et al. |
| 6,932,837 B2 | 8/2005 | Amplatz et al. |
| 6,936,058 B2 | 8/2005 | Forde et al. |
| 6,979,343 B2 | 12/2005 | Russo et al. |
| 7,033,372 B1 | 4/2006 | Cahalan |
| 7,037,329 B2 | 5/2006 | Martin |
| 7,044,134 B2 | 5/2006 | Khairkhahan et al. |
| 7,097,653 B2 | 8/2006 | Freudenthal et al. |
| 7,105,024 B2 | 9/2006 | Richelsoph |
| 7,144,410 B2 | 12/2006 | Marino et al. |
| 7,226,466 B2 | 6/2007 | Opolski |
| 7,309,341 B2 | 12/2007 | Ortiz et al. |
| 7,317,951 B2 | 1/2008 | Schneider et al. |
| 7,338,514 B2 | 3/2008 | Wahr et al. |
| 7,350,995 B1 | 4/2008 | Rhodes |
| 7,419,498 B2 | 9/2008 | Opolski et al. |
| 7,445,630 B2 | 11/2008 | Lashinski et al. |
| 7,473,266 B2 | 1/2009 | Glaser |
| 7,485,141 B2 | 2/2009 | Majercak et al. |
| 7,530,995 B2 | 5/2009 | Quijano et al. |
| 7,611,534 B2 | 11/2009 | Kapadia et al. |
| 7,625,392 B2 | 12/2009 | Coleman et al. |
| 7,658,747 B2 | 2/2010 | Forde et al. |
| 7,678,123 B2 | 3/2010 | Chanduszko |
| 7,691,144 B2 | 4/2010 | Chang et al. |
| 7,699,297 B2 | 4/2010 | Cicenas et al. |
| 7,704,268 B2 | 4/2010 | Chanduszko |
| 7,722,629 B2 | 5/2010 | Chambers |
| 7,758,589 B2 | 7/2010 | Ortiz et al. |
| 7,842,026 B2 | 11/2010 | Cahill et al. |
| 7,860,579 B2 | 12/2010 | Goetzinger et al. |
| 7,871,419 B2 | 1/2011 | Devellian et al. |
| 7,905,901 B2 | 3/2011 | Corcoran et al. |
| 7,967,769 B2 | 6/2011 | Faul et al. |
| 7,976,564 B2 | 7/2011 | Blaeser et al. |
| 8,010,186 B1 | 8/2011 | Ryu |
| 8,021,359 B2 | 9/2011 | Auth et al. |
| 8,034,061 B2 | 10/2011 | Amplatz et al. |
| 8,043,360 B2 | 10/2011 | McNamara et al. |
| 8,048,147 B2 | 11/2011 | Adams |
| 8,052,750 B2 | 11/2011 | Tuval et al. |
| 8,157,860 B2 | 4/2012 | McNamara et al. |
| 8,163,004 B2 | 4/2012 | Amplatz et al. |
| 8,172,896 B2 | 5/2012 | McNamara et al. |
| 8,252,042 B2 | 8/2012 | McNamara et al. |
| 8,303,623 B2 | 11/2012 | Meizer et al. |
| 8,313,505 B2 | 11/2012 | Amplatz et al. |
| 8,361,138 B2 | 1/2013 | Adams |
| 8,366,088 B2 | 2/2013 | Allen et al. |
| 8,398,670 B2 | 3/2013 | Amplatz et al. |
| 8,460,372 B2 | 6/2013 | McNamara et al. |
| 8,696,611 B2 | 4/2014 | Nitzan et al. |
| 8,696,693 B2 | 4/2014 | Najafi et al. |
| 8,740,962 B2 | 6/2014 | Finch et al. |
| 8,745,845 B2 | 6/2014 | Finch et al. |
| 8,747,453 B2 | 6/2014 | Amplatz et al. |
| 8,752,258 B2 | 6/2014 | Finch et al. |
| 8,777,974 B2 | 7/2014 | Amplatz et al. |
| 8,778,008 B2 | 7/2014 | Amplatz et al. |
| 8,864,822 B2 | 10/2014 | Spence et al. |
| 8,882,697 B2 | 11/2014 | Celermajer et al. |
| 8,951,223 B2 | 2/2015 | McNamara et al. |
| 8,979,923 B2 | 3/2015 | Spence et al. |
| 9,005,155 B2 | 4/2015 | Sugimoto |
| 9,205,236 B2 | 12/2015 | McNamara et al. |
| 9,232,997 B2 | 1/2016 | Sugimoto et al. |
| 9,277,995 B2 | 3/2016 | Celermajer et al. |
| 9,358,371 B2 | 6/2016 | McNamara et al. |
| 9,445,797 B2 | 9/2016 | Rothstein et al. |
| 9,456,812 B2 | 10/2016 | Finch et al. |
| 9,681,948 B2 | 6/2017 | Levi et al. |
| 9,724,499 B2 | 8/2017 | Rottenberg et al. |
| 2001/0027287 A1 | 10/2001 | Shmulewitz et al. |
| 2001/0029368 A1 | 10/2001 | Berube |
| 2001/0053932 A1 | 12/2001 | Phelps et al. |
| 2002/0033180 A1 | 3/2002 | Solem |
| 2002/0077698 A1 | 6/2002 | Peredo |
| 2002/0082525 A1 | 6/2002 | Oslund et al. |
| 2002/0082613 A1 | 6/2002 | Hathaway et al. |
| 2002/0095172 A1 | 7/2002 | Mazzocchi et al. |
| 2002/0120277 A1 | 8/2002 | Hauschild et al. |

(56) References Cited

U.S. PATENT DOCUMENTS

| | | |
|---|---|---|
| 2002/0143289 A1 | 10/2002 | Ellis et al. |
| 2002/0161424 A1 | 10/2002 | Rapacki et al. |
| 2002/0161432 A1 | 10/2002 | Mazzucco et al. |
| 2002/0165606 A1 | 11/2002 | Wolf et al. |
| 2002/0169377 A1 | 11/2002 | Khairkhahan et al. |
| 2002/0173742 A1 | 11/2002 | Keren et al. |
| 2002/0177894 A1 | 11/2002 | Acosta et al. |
| 2002/0183826 A1 | 12/2002 | Dorn et al. |
| 2003/0032967 A1 | 2/2003 | Park et al. |
| 2003/0093072 A1 | 5/2003 | Friedman |
| 2003/0125798 A1 | 7/2003 | Martin |
| 2004/0044351 A1 | 3/2004 | Searle |
| 2004/0078950 A1 | 4/2004 | Schreck |
| 2004/0087937 A1 | 5/2004 | Eggers et al. |
| 2004/0093075 A1 | 5/2004 | Kuehne |
| 2004/0102719 A1 | 5/2004 | Keith et al. |
| 2004/0102797 A1 | 5/2004 | Golden et al. |
| 2004/0111095 A1 | 6/2004 | Gordon et al. |
| 2004/0133236 A1 | 7/2004 | Chanduszko |
| 2004/0143261 A1 | 7/2004 | Hartley et al. |
| 2004/0143262 A1 | 7/2004 | Visram et al. |
| 2004/0143292 A1 | 7/2004 | Marino et al. |
| 2004/0162514 A1 | 8/2004 | Alferness et al. |
| 2004/0176788 A1 | 9/2004 | Opolski |
| 2004/0193261 A1 | 9/2004 | Berreklouw |
| 2004/0206363 A1 | 10/2004 | McCarthy et al. |
| 2004/0220653 A1 | 11/2004 | Borg et al. |
| 2004/0236308 A1 | 11/2004 | Herweck et al. |
| 2004/0243143 A1 | 12/2004 | Corcoran et al. |
| 2004/0267306 A1 | 12/2004 | Blaeser et al. |
| 2005/0015953 A1 | 1/2005 | Keidar |
| 2005/0049692 A1 | 3/2005 | Numamoto et al. |
| 2005/0049697 A1 | 3/2005 | Sievers |
| 2005/0065507 A1 | 3/2005 | Hartley et al. |
| 2005/0065546 A1 | 3/2005 | Corcoran et al. |
| 2005/0065548 A1 | 3/2005 | Marino et al. |
| 2005/0070934 A1 | 3/2005 | Tanaka et al. |
| 2005/0075655 A1 | 4/2005 | Bumbalough et al. |
| 2005/0075665 A1 | 4/2005 | Brenzel et al. |
| 2005/0080400 A1 | 4/2005 | Corcoran et al. |
| 2005/0080430 A1 | 4/2005 | Wright et al. |
| 2005/0096735 A1 | 5/2005 | Hojeibane et al. |
| 2005/0113868 A1 | 5/2005 | Devellian et al. |
| 2005/0131503 A1 | 6/2005 | Solem |
| 2005/0137609 A1 | 6/2005 | Guiraudon |
| 2005/0137686 A1 | 6/2005 | Salahieh et al. |
| 2005/0148925 A1 | 7/2005 | Rottenberg et al. |
| 2005/0159738 A1 | 7/2005 | Visram et al. |
| 2005/0165344 A1* | 7/2005 | Dobak, III ............... A61F 2/01 604/8 |
| 2005/0187616 A1 | 8/2005 | Realyvasquez |
| 2005/0234537 A1 | 10/2005 | Edin |
| 2005/0240205 A1 | 10/2005 | Berg et al. |
| 2005/0251063 A1 | 11/2005 | Basude |
| 2005/0251187 A1 | 11/2005 | Beane et al. |
| 2005/0267524 A1 | 12/2005 | Chanduszko |
| 2005/0273075 A1 | 12/2005 | Krulevitch et al. |
| 2005/0273124 A1 | 12/2005 | Chanduszko |
| 2005/0288722 A1 | 12/2005 | Eigler et al. |
| 2006/0004323 A1 | 1/2006 | Chang et al. |
| 2006/0009800 A1 | 1/2006 | Christianson et al. |
| 2006/0009832 A1 | 1/2006 | Fisher |
| 2006/0041183 A1 | 2/2006 | Massen et al. |
| 2006/0052821 A1 | 3/2006 | Abbott |
| 2006/0085060 A1 | 4/2006 | Campbell |
| 2006/0095066 A1 | 5/2006 | Chang et al. |
| 2006/0111704 A1 | 5/2006 | Brenneman et al. |
| 2006/0122646 A1 | 6/2006 | Corcoran et al. |
| 2006/0122647 A1 | 6/2006 | Callaghan et al. |
| 2006/0135990 A1 | 6/2006 | Johnson |
| 2006/0136043 A1 | 6/2006 | Cully et al. |
| 2006/0155305 A1 | 7/2006 | Freudenthal et al. |
| 2006/0184088 A1 | 8/2006 | Van Bibber et al. |
| 2006/0210605 A1 | 9/2006 | Chang et al. |
| 2006/0217761 A1 | 9/2006 | Opolski |
| 2006/0224183 A1* | 10/2006 | Freudenthal ....... A61B 17/0057 606/213 |
| 2006/0241675 A1* | 10/2006 | Johnson ................... A61F 2/01 606/200 |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0259121 A1 | 11/2006 | Osypka |
| 2006/0276882 A1 | 12/2006 | Case et al. |
| 2007/0005127 A1 | 1/2007 | Boekstegers et al. |
| 2007/0010851 A1 | 1/2007 | Chanduszko et al. |
| 2007/0021739 A1 | 1/2007 | Weber |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088375 A1 | 4/2007 | Beane et al. |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0129755 A1 | 6/2007 | Abbott et al. |
| 2007/0168018 A1 | 7/2007 | Amplatz et al. |
| 2007/0185513 A1 | 8/2007 | Woolfson et al. |
| 2007/0197952 A1 | 8/2007 | Stiger |
| 2007/0198060 A1 | 8/2007 | Devellian et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033478 A1 | 2/2008 | Meng |
| 2008/0033543 A1 | 2/2008 | Gurskis et al. |
| 2008/0039804 A1 | 2/2008 | Edmiston et al. |
| 2008/0039881 A1 | 2/2008 | Greenberg |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0109069 A1 | 5/2008 | Coleman et al. |
| 2008/0119891 A1 | 5/2008 | Miles et al. |
| 2008/0125861 A1 | 5/2008 | Webler et al. |
| 2008/0154250 A1 | 6/2008 | Makower et al. |
| 2008/0154302 A1 | 6/2008 | Opolski et al. |
| 2008/0154351 A1 | 6/2008 | Leewood et al. |
| 2008/0154355 A1 | 6/2008 | Benichou et al. |
| 2008/0161901 A1 | 7/2008 | Heuser et al. |
| 2008/0172123 A1 | 7/2008 | Yadin |
| 2008/0177381 A1 | 7/2008 | Navia et al. |
| 2008/0183279 A1 | 7/2008 | Bailey et al. |
| 2008/0188880 A1 | 8/2008 | Fischer et al. |
| 2008/0188888 A1 | 8/2008 | Adams et al. |
| 2008/0215008 A1 | 9/2008 | Nance et al. |
| 2008/0221582 A1 | 9/2008 | Gia et al. |
| 2008/0228264 A1 | 9/2008 | Li et al. |
| 2008/0249397 A1 | 10/2008 | Kapadia |
| 2008/0249562 A1 | 10/2008 | Cahill |
| 2008/0249612 A1 | 10/2008 | Osborne et al. |
| 2008/0262592 A1 | 10/2008 | Jordan et al. |
| 2008/0269662 A1 | 10/2008 | Vassiliades et al. |
| 2008/0312679 A1 | 12/2008 | Hardert et al. |
| 2009/0018570 A1 | 1/2009 | Righini et al. |
| 2009/0030495 A1 | 1/2009 | Koch |
| 2009/0054805 A1 | 2/2009 | Boyle |
| 2009/0054982 A1* | 2/2009 | Cimino ..................... A61F 2/08 623/13.19 |
| 2009/0054984 A1 | 2/2009 | Shortkroff et al. |
| 2009/0062841 A1 | 3/2009 | Amplatz et al. |
| 2009/0076541 A1 | 3/2009 | Chin et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal |
| 2009/0112251 A1 | 4/2009 | Qian et al. |
| 2009/0171386 A1 | 7/2009 | Amplatz et al. |
| 2009/0177269 A1 | 7/2009 | Kalmann et al. |
| 2009/0187214 A1 | 7/2009 | Amplatz et al. |
| 2009/0209855 A1 | 8/2009 | Drilling et al. |

(56) References Cited

U.S. PATENT DOCUMENTS

| | | |
|---|---|---|
| 2009/0209999 A1 | 8/2009 | Afremov |
| 2009/0234443 A1 | 9/2009 | Ottma et al. |
| 2009/0264991 A1 | 10/2009 | Paul et al. |
| 2009/0270840 A1 | 10/2009 | Miles et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030259 A1 | 2/2010 | Pavcnik et al. |
| 2010/0030321 A1 | 2/2010 | Mach |
| 2010/0049307 A1 | 2/2010 | Ren |
| 2010/0051886 A1 | 3/2010 | Cooke et al. |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0114140 A1 | 5/2010 | Chanduszko |
| 2010/0121370 A1 | 5/2010 | Kariniemi |
| 2010/0131053 A1 | 5/2010 | Agnew |
| 2010/0211046 A1 | 8/2010 | Adams et al. |
| 2010/0249490 A1 | 9/2010 | Farnan |
| 2010/0249491 A1 | 9/2010 | Farnan et al. |
| 2010/0268316 A1 | 10/2010 | Brenneman et al. |
| 2010/0274351 A1 | 10/2010 | Rolando et al. |
| 2010/0298755 A1 | 11/2010 | McNamara et al. |
| 2010/0305685 A1 | 12/2010 | Millwee et al. |
| 2010/0324588 A1 | 12/2010 | Miles et al. |
| 2011/0004296 A1 | 1/2011 | Lutter et al. |
| 2011/0022079 A1 | 1/2011 | Miles et al. |
| 2011/0040374 A1 | 2/2011 | Goetz et al. |
| 2011/0071623 A1 | 3/2011 | Finch et al. |
| 2011/0087261 A1 | 4/2011 | Wittkampf et al. |
| 2011/0093062 A1 | 4/2011 | Cartledge et al. |
| 2011/0106149 A1 | 5/2011 | Ryan et al. |
| 2011/0130784 A1 | 6/2011 | Kusleika |
| 2011/0184439 A1 | 7/2011 | Anderson et al. |
| 2011/0213364 A1 | 9/2011 | Davis et al. |
| 2011/0218479 A1 | 9/2011 | Rottenberg et al. |
| 2011/0257723 A1 | 10/2011 | McNamara |
| 2011/0270239 A1 | 11/2011 | Werneth |
| 2011/0295183 A1 | 12/2011 | Finch et al. |
| 2011/0319806 A1 | 12/2011 | Wardle |
| 2011/0319989 A1 | 12/2011 | Lane et al. |
| 2012/0022427 A1 | 1/2012 | Kapadia |
| 2012/0130301 A1 | 5/2012 | McNamara et al. |
| 2012/0165928 A1 | 6/2012 | Nitzan et al. |
| 2012/0265296 A1 | 10/2012 | McNamara et al. |
| 2012/0289882 A1 | 11/2012 | McNamara et al. |
| 2012/0289971 A1 | 11/2012 | Segermark et al. |
| 2012/0290062 A1 | 11/2012 | McNamara et al. |
| 2012/0290077 A1 | 11/2012 | Aklog et al. |
| 2012/0316597 A1 | 12/2012 | Fitz et al. |
| 2013/0030521 A1 | 1/2013 | Nitzan et al. |
| 2013/0041359 A1 | 2/2013 | Asselin et al. |
| 2013/0165967 A1 | 6/2013 | Amin et al. |
| 2013/0178784 A1 | 7/2013 | McNamara et al. |
| 2013/0204175 A1* | 8/2013 | Sugimoto .......... A61M 27/002 604/8 |
| 2013/0253546 A1* | 9/2013 | Sander .................. A61B 17/11 606/151 |
| 2013/0267885 A1 | 10/2013 | Celermajer et al. |
| 2013/0281988 A1 | 10/2013 | Magin et al. |
| 2014/0012181 A1 | 1/2014 | Sugimoto et al. |
| 2014/0172074 A1* | 6/2014 | Concagh .................. A61F 2/90 623/1.19 |
| 2014/0194971 A1 | 7/2014 | McNamara |
| 2014/0257167 A1 | 9/2014 | Celermajer et al. |
| 2014/0277045 A1 | 9/2014 | Fazio et al. |
| 2014/0277054 A1 | 9/2014 | McNamara et al. |
| 2015/0039084 A1 | 2/2015 | Levi et al. |
| 2015/0119796 A1 | 4/2015 | Finch |
| 2015/0148731 A1 | 5/2015 | McNamara et al. |
| 2015/0313599 A1 | 11/2015 | Johnson et al. |
| 2016/0022423 A1 | 1/2016 | McNamara et al. |
| 2016/0022970 A1 | 1/2016 | Forcucci et al. |
| 2016/0051800 A1 | 2/2016 | Vassiliades et al. |
| 2016/0120550 A1 | 5/2016 | McNamara et al. |
| 2016/0135813 A1 | 5/2016 | Johnson et al. |
| 2016/0166381 A1 | 6/2016 | Sugimoto et al. |
| 2016/0184561 A9 | 6/2016 | McNamara et al. |
| 2017/0273790 A1 | 9/2017 | Vettukattil et al. |
| 2018/0256865 A1 | 9/2018 | Finch et al. |
| 2019/0021861 A1 | 1/2019 | Finch |

FOREIGN PATENT DOCUMENTS

| | | |
|---|---|---|
| CN | 1582136 A | 2/2005 |
| CN | 1780589 A | 5/2006 |
| CN | 101035481 A | 9/2007 |
| CN | 101035488 A | 9/2007 |
| CN | 101292889 A | 10/2008 |
| CN | 101426431 A | 5/2009 |
| CN | 101579267 A | 11/2009 |
| EP | 1264582 A2 | 2/2002 |
| EP | 1480565 A1 | 9/2003 |
| EP | 1470785 A1 | 10/2004 |
| EP | 1849440 A1 | 10/2007 |
| FR | 2827153 A1 | 1/2003 |
| JP | 58-27935 U | 6/1983 |
| JP | H02-277459 A | 11/1990 |
| JP | 2003530143 | 10/2003 |
| WO | WO95/27448 A1 | 10/1995 |
| WO | WO98/08456 A1 | 3/1998 |
| WO | WO98/42403 A1 | 10/1998 |
| WO | WO01/15618 A2 | 3/2001 |
| WO | WO02/094363 A2 | 11/2002 |
| WO | WO2004/019811 A2 | 3/2004 |
| WO | WO2005/048881 A1 | 6/2005 |
| WO | WO2005/048883 A1 | 6/2005 |
| WO | WO2006/127765 A1 | 11/2006 |
| WO | WO2007/054116 A | 5/2007 |
| WO | WO2007/083288 A2 | 7/2007 |
| WO | WO2008/058940 A1 | 5/2008 |
| WO | WO2010/111666 A1 | 9/2010 |
| WO | WO2010/129511 A2 | 11/2010 |

OTHER PUBLICATIONS

Althoff et al.; Long-term follow up of a fenestrated amplatzer atrial septal occluder in pulmonary arterial hypertension; Chest; 133(1); pp. 183-185; Jan. 2008.

Atz et al.; Preoperative management of pulmonary venous hypertension in hypoplastic left heart syndrome with restrictive atrial septal defect; The American Journal of Cardiology; 83; pp. 1224-1228; Apr. 15, 1999.

Bailey, Steven R.; Nanotechnology in prosthetic heart valves (presentation); 31 pgs.; (year of pub. sufficiently earlier than effective US filing date and any foreign priority date) 2005.

Bolling, Steven; Direct flow medical—My valve is better (presentation); 21 pgs.; Apr. 23, 2009.

Cheatham, John P.; Intervention in the critically ill neonate and infant with hypoplastic left heart syndrome and intact atrial septum; Journal of Interventional Cardiology; 14(3); pp. 357-366; Jun. 2001.

Coselli, Joseph S.; No! Valve replacement: Patient prosthetic mismatch rarely occurs (presentation); 75 pgs.; Apr. 25, 2009.

Design News; Low power piezo motion; retrieved from the Internet (http://www.designnews.com/document.asp?doc_id=229053 &dfpPParams=ht_13,aid_229053&dfpLayout=article); 3 pgs.; May 14, 2010.

Gaudiani et al.; A philosophical approach to mirral valve repair (presentation); 28 pgs.; Apr. 24, 2009.

Hijazi, Zayad M.; Valve implantation (presentation); 36 pgs.; May 10, 2007.

Larios et al.; The use of an artificial foraminal valve prosthesis in the closure of interatrial and interventricular septal defects; Chest; 36(6); pp. 631-641; Dec. 1959.

Leon, Martin B.; Transcatheter aortic valve therapy: Summary thoughts (presentation); 19 pgs.; Jun. 24, 2009.

Ling et al.; Implantable magnetic relaxation sensors measure cumulative exposure to cardiac biomarkers; Nat Biotechnol; 29(3); pp. 273-277; Mar. 2011.

(56) References Cited

OTHER PUBLICATIONS

McMahon, Jim; Piezo motors and actuators: Streamlining medical device performance; Designfax; Mar. 23, 2010; 5 pgs.; retrieved from the Internet on Jul. 19, 2012 (http://www.designfax.net/enews/20100323/feature-1.asp).

Merchant et al.; Advances in arrhythmia and electrophysiology; implantable sensors for heart failure; Cir Arrhythm Electrophysiol; 3; pp. 657-667; Dec. 2010.

Moses, Jeffrey W.; The good, the bad and the ugly of transcatheter AVR (presentation); 28 pgs.; Jul. 10, 2009.

O'Loughlin et al.; Insertion of a fenestrated amplatzer atrial sestosotomy device for severe pulmonary hypertension; Heart Lung Circ.; 15(4); pp. 275-277; Aug. 2006.

Park et al.; Blade atrial septostomy: Collaborative study; Circulation; 66 (2); pp. 258-266; Aug. 1982.

Pedra et al.; Stent implantation to create interatrial communications in patients with complex congenital heart disease; Catheterization and Cardiovascular Interventions; 47; pp. 310-313; Jan. 27, 1999.

Perry et al.; Creation and maintenance of an adequate interatrial communication in left atrioventricular valve atresia or stenosis; The American Journal of Cardiology; 58; pp. 622-626; Sep. 15, 1986.

Philips et al.; Ventriculofemoroatrial shunt: A viable alternative for the treatment of hydrocephalus; J. Neurosurg.; 86; pp. 1063-1066; Jun. 1997.

Physik Instrumente; Piezo for Motion Control in Medical Design and Drug Research (product information); Physik Instrumente (PI) GmbH & Co. KG; 22 pgs.; © Nov. 21, 2010.

Roven et al.; Effect of compromising right ventricular function in left ventricular failure by means of interatrial and other shunts; Am J Cardiol.; 24(2); pp. 209-219; Aug. 1969.

RPI Newswire; Implantable, wireless sensors share secrets of healing tissues; RPI Newswire; 1 pg.; Feb. 21, 2012; retrieved from the Internet on Jul. 18, 2012 (http://news.rpi.edu/update.do).

Sambhi et al.; Pathologic Physiology of Lutembacher Syndrome; Am J Cardiol.; 2(6); pp. 681-686; Dec. 1958.

Sommer et al.; Transcatheter creation of atrial septal defect and fontan fenestration with "butterfly" stent technique; Journal of the American college of Cardiology; 33(2); Suppl. A; 3 pgs.; Feb. 1999.

Stone, Gregg W.; Transcatheter devices for mirral valve repair, surveying the landscape (presentation); 48 pgs.; Jul. 10, 2009.

Stormer et al.; Comparative study of in vitro flow characteristics between a human aortic valve and a designed aortic valve and six corresponding types of prosthetic heart valves; Eur Surg Res; 8(2); pp. 117-131; (year of pub. sufficiently earlier than effective US filing date and any foreign priority date) 1976.

Trafton, Anne; Detecting whether a heart attack has occurred; MIT News; 3 pgs.; Feb. 14, 2011; retrieved from the internet Sep. 20, 2014 (http://newsoffice.mit.edu/2011/cardiac-implant-0214).

Watterson et al.; Very small pulmonary arteries: Central end-to-side shunt; Ann. Thorac. Surg.; 52(5); pp. 1132-1137; Nov. 1991.

Webber, Ralph; Piezo Motor Based Medical Devices; Medical Design Technology; 5 pgs.; Apr. 2, 2009; retrieved from the Internet on Jul. 19, 2012 (http://mdtmag.com/articles/2009/04/piezo-motor-based-medical-devices).

Celermajer et at.; U.S. Appl. No. 14/498,903 entitled "Apparatus and methods to create and maintain an intra-atrial pressure relief opening," filed Sep. 26, 2014.

Forcucci et al.; U.S. Appl. No. 15/346,711 entitled "Retrievable devices for treating heart failure," filed Nov. 8, 2016.

\* cited by examiner

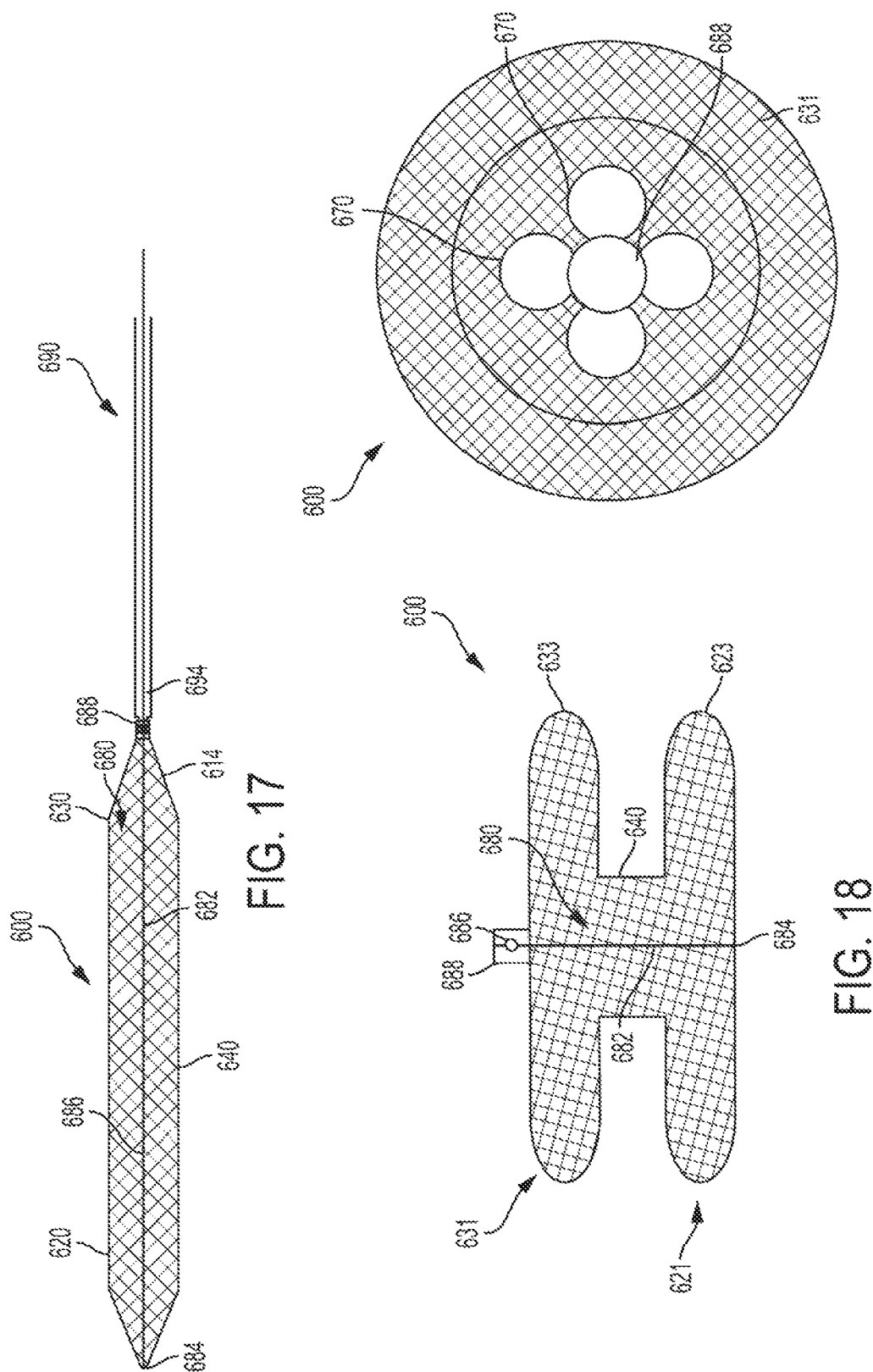

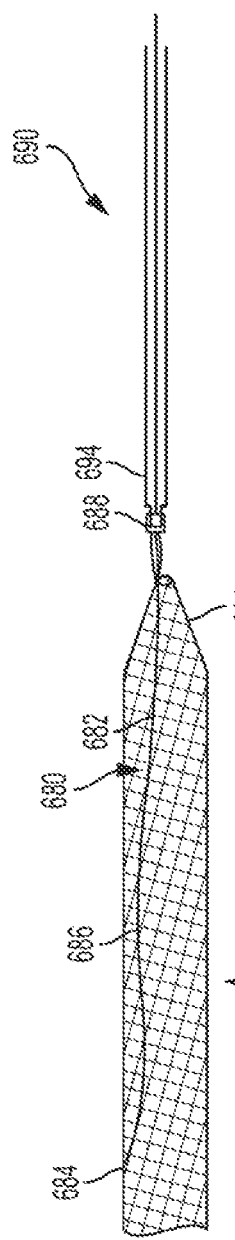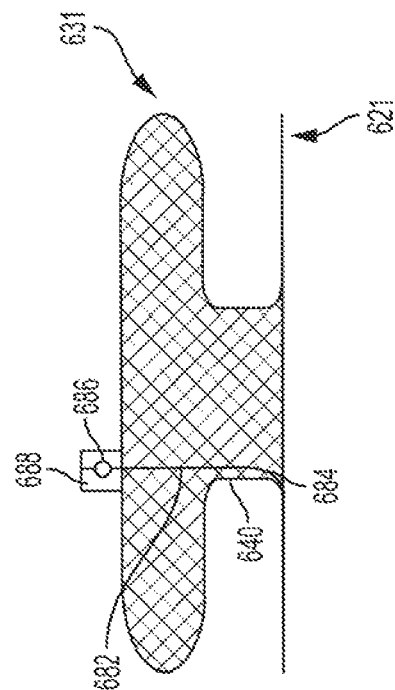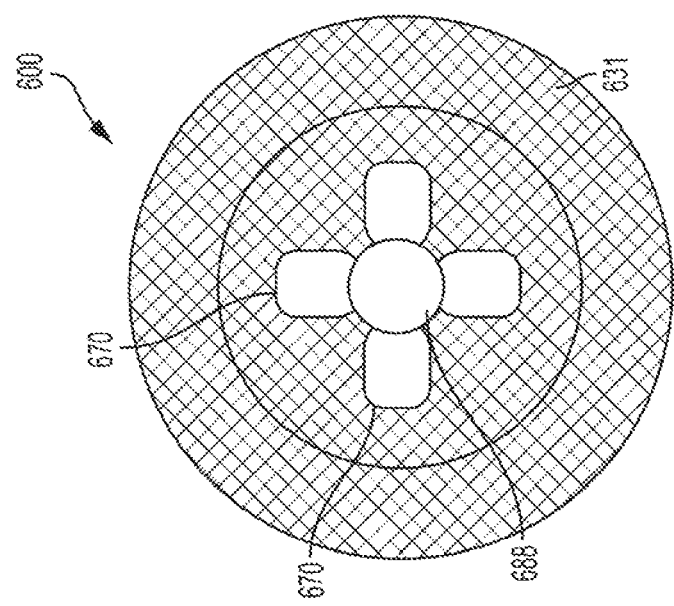
FIG. 20
FIG. 21
FIG. 19B

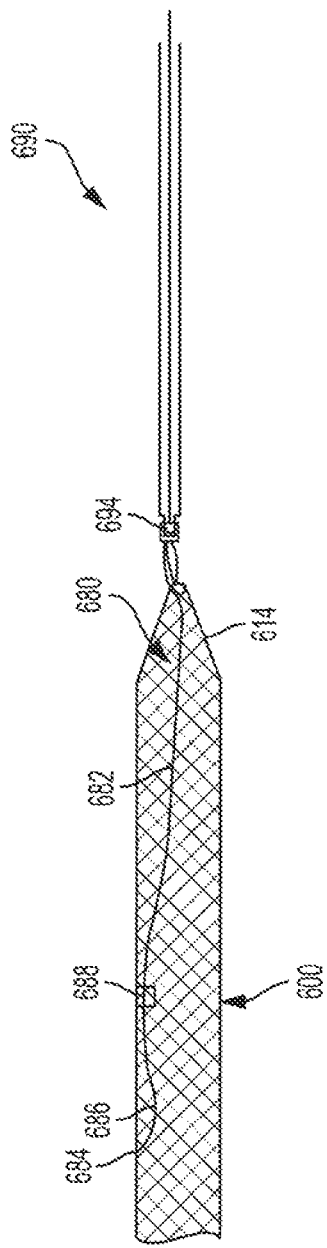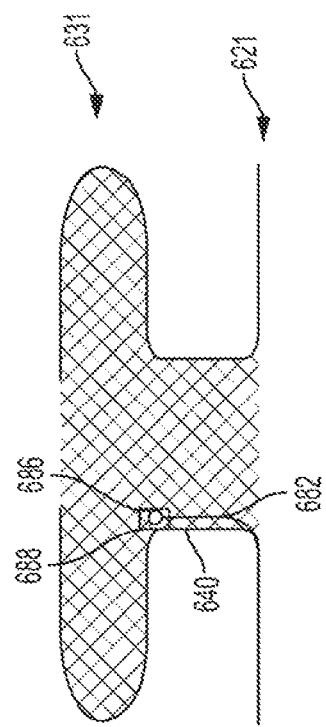

DEVICES AND METHODS FOR TREATING HEART FAILURE

CROSS REFERENCE TO RELATED APPLICATION

This application claims the benefit of and priority to U.S. Provisional Application No. 61/952,113, filed on Mar. 12, 2014, the entirety of which is incorporated herein by reference.

FIELD

The present teachings relate to devices and methods of use thereof for treating heart failure. An aspect of the present teachings relates to a device that can be used to change (e.g., reduce) the blood pressure in a heart chamber, for example, by creating a shunt and optionally regulating the flow of blood through the shunt in order to enhance the therapeutic effect of the shunt. The present teachings further relate to a method of utilizing such a device, for example, in treating congestive heart failure related conditions, for example, acute cardiogenic pulmonary edema caused by an elevated pressure in a left side chamber in the heart.

BACKGROUND

Congestive heart failure (CHF) is a condition that affects millions of people worldwide. CHF results from a weakening or stiff of the heart muscle that commonly is caused by myocardial ischemia (due to, e.g., myocardial infarction) or cardiomyopathy (e.g., myocarditis, amyloidosis). CHF causes a reduced cardiac output and inadequate blood to meet the needs of body tissues.

Treatments for CHF include: (1) pharmacological treatments, (2) assisting systems, and (3) surgical treatments. Pharmacological treatments, e.g., with diuretics, are used to reduce the workload of a heart by reducing blood volume and preload. While pharmacological treatments can improve quality of life, they have little effect on survival. Assisting devices, e.g., mechanical pumps, are used to reduce the load on a heart by performing all or part of the pumping function normally done by the heart. However, in a chronic ischemic heart, high-rate pacing may lead to an increased diastolic pressure, calcium overload, and damages to the muscle fibers. There are at least three surgical procedures for treating a heart failure; (1) heart transplant, (2) dynamic cardiomyoplasty, and (3) the Batista partial left ventriculectomy. These surgical treatments are invasive and have many limitations.

CHF is generally classified into systolic heart failures (SHF) or diastolic heart failures (DHF). In a SHF, the pumping action of a heart is reduced or weakened. A normal ejection fraction (EF), the volume of blood ejected out of the left ventricle (stroke volume) divided by the maximum volume remaining in the left ventricle at the end of the diastole or relaxation phase, is greater than 50%. In a systolic heart failure, EF is decreased to less than 50%. A patient with SHF may have an enlarged left ventricle because of cardiac remodeling developed to maintain an adequate stroke-volume. This pathophysiological phenomenon is often associated with an increased atrial pressure and an increased left ventricular filling pressure.

DHF is a heart failure without any major valve disease even though the systolic function of the left ventricle is preserved. Generally, DHF is a failure of the ventricle to adequately relax and expand, resulting in a decrease in the stroke volume of the heart. Presently, there are very few treatment options for patients suffering from DHF. DHF afflicts between 30% and 70% of patients with CHF.

There are several known techniques that can be used to treat the symptoms of DHF. Without attempting to characterize the following references, for example. U.S. Pat. No. 8,091,556 by Keren et al. discloses the use of an interatrial pressure relief shunt with a valve and a tissue affixation element at each end of the shunt; and United States Patent Application Publication No. 20050165344 by Dobak discloses a pressure relief system with an interatrial septal conduit with an emboli barrier or trap mechanism to prevent cryptogenic stroke due to thrombi or emboli crossing the conduit into the left sided circulation. Dobak also discloses a conduit with a one-way valve which directs blood flow from the left atrium to the right atrium.

The constantly evolving nature of heart failures represents a significant challenge for the treatment. Therefore, there is a need for novel and adaptable methods and devices for treating DHF, for example, by creating a pressure relief shunt which can be retrieved, repositioned, adjusted, expanded, contracted, occluded, sealed and/or otherwise altered as required to treat a patient. Furthermore, there exists a need for treating DHF with devices and methods that can self-adjust over time either in accordance with or in anticipation of the gradual hemodynamic changes associated with a heart failure.

SUMMARY

An aspect of the present teachings provides an implantable medical device having a braided structure. In various embodiments, the device is unitary in construction. In various embodiments, the device comprises a shunt portion, a distal retention flange, and a proximal retention flange. In various embodiments, the shunt portion has a distal end, a proximal end, and a tubular body allowing blooding flowing through. In various embodiments, the distal retention flange has a free end and a fixed end. In various embodiments, the fixed end of the distal retention flange connects to the distal end of the shunt portion. In various embodiments, the free end of the distal retention flange extending radially outward from the fixed end of the distal retention flange. In various embodiments, the proximal retention flange also has a free end and a fixed end. In various embodiments, the fixed end of the proximal retention flange connecting to the proximal end of the shunt portion. In various embodiments, the free end of the proximal retention flange extends radially outward from the fixed end of the proximal retention flange. In various embodiments, the shunt portion has a first hoop stiffness. In various embodiments, the distal retention flange has a second hoop stiffness. In various embodiments, the proximal retention flange has a third hoop stiffness. In various embodiments, the first hoop stiffness is greater than at least one of the second and third hoop stiffness.

An aspect of the present teachings provides an implantable medical device having a braided structure. In various embodiments, the device is unitary in construction. In various embodiments, the device comprises a shunt portion, a distal retention flange, and a proximal retention flange. In various embodiments, the shunt portion has a distal end, a proximal end, and a tubular body allowing blooding flowing through. In various embodiments, the distal retention flange has a free end and a fixed end. In various embodiments, the fixed end of the distal retention flange connects to the distal end of the shunt portion. In various embodiments, the free end of the distal retention flange extending radially outward from the fixed end of the distal retention flange. In various embodiments, the proximal retention flange also has a free end and a fixed end. In various embodiments, the fixed end of the proximal retention flange connecting to the proximal end of the shunt portion. In various embodiments, the free end of the proximal retention flange extends radially outward from the fixed end of the proximal retention flange. In various embodiments, the shunt portion has a first braid angle. In various embodiments, the distal retention flange has a second braid angle. In various embodiments, the proximal retention flange has a third braid angle. In various embodiments, the first braid angle is greater than at least one of the second and third braid angle.

An aspect of the present teachings provides an implantable medical device having a braided structure. In various embodiments, the device is unitary in construction. In various embodiments, the device comprises a shunt portion, a distal retention flange and a proximal retention flange. In various embodiments, the shunt portion has a distal end, a proximal end, and a tubular body allowing blooding flowing through. In various embodiments, the distal retention flange has a free end and a fixed end. In various embodiments, the fixed end of the distal retention flange connects to the distal end of the shunt portion. In various embodiments, the free end of the distal retention flange extending radially outward from the fixed end of the distal retention flange. In various embodiments, the proximal retention flange also has a free end and a fixed end. In various embodiments, the fixed end of the proximal retention flange connecting to the proximal end of the shunt portion. In various embodiments, the free end of the proximal retention flange connects to a proximal hub. In various embodiments, the shunt portion has a first hoop stiffness. In various embodiments, the distal retention flange has a second hoop stiffness. In various embodiments, the proximal retention flange has a third hoop stiffness. In various embodiments, the first hoop stiffness is greater than at least one of the second and third hoop stiffness.

An aspect of the present teachings provides an implantable medical device having a braided structure. In various embodiments, the device is unitary in construction. In various embodiments, the device comprises a shunt portion, a distal retention flange and a proximal retention flange. In various embodiments, the shunt portion has a distal end, a proximal end, a tubular body allowing blooding flowing through, a first diameter, and a braid angle. In various embodiments, the distal retention flange has a free end, a fixed end, and a second diameter. In various embodiments, the fixed end of the distal retention flange connects to the distal end of the shunt portion. In various embodiments, the free end of the distal retention flange extending radially outward from the fixed end of the distal retention flange. In various embodiments, the proximal retention flange also has a free end, a fixed end, and a second diameter. In various embodiments, the fixed end of the proximal retention flange connecting to the proximal end of the shunt portion. In various embodiments, the ratio of the second or the third diameter to the first diameter equals or is greater than $1/\sin \theta$.

An aspect of the present teachings provides an implantable medical device having a braided structure. In various embodiments, the device comprises a shunt portion, a distal retention flange, and a proximal retention flange. In various embodiments, the device comprises an elongated configuration. In various embodiments, the device comprises an expanded configuration. In various embodiments, the shunt portion has a distal end, a proximal end, and a tubular body connecting with the distal end and the proximal end. In various embodiments, the shunt portion has a delivery length and a deployment length. In some embodiments, the delivery length is greater than the deployment length. In some embodiments, the delivery length is the same as the deployment length. In various embodiments, the shunt portion has a delivery diameter. In various embodiments, the shunt portion has a deployment diameter. In some embodiments, the delivery diameter is equal to or small than the deployment diameter.

In various embodiments, the device comprises a constraint. Without limiting the present teachings to any particular theory, one or more than one constraints can be used to change at least one mechanical property of the device, including the shunt portion, the distal retention flange, and/or the proximal retention flange. In some embodiments, the constraint increases the stiffness of the shunt portion of the device. In some embodiments, the constraint increases the stiffness of the distal retention flange. In some embodiments, the constraint increases the stiffness of the proximal retention flange.

In various embodiments, the constraint includes an axial constraining wire. In some embodiments, the axial constraining wire is attached, removably in particular embodiments, to the device. In particular embodiments, the axial constraining wire is attached to the distal retention flange. In particular embodiments, the axial constraining wire is attached to the shunt portion. In particular embodiments, the axial constraining wire is attached to the proximal retention flange.

In various embodiments, the constraint includes a locking feature and a lock receiver. In various other embodiments, the constraint includes another mechanism that performs the same function in substantially the same way to yield substantially same results. In some embodiments, the locking feature is connected with the axial constraining wire. In particular embodiments, the connection between the locking feature and the axial constraining wire is adjustable. In some embodiments, the lock receiver is attached to the device. In particular embodiments, the lock receiver is attached to the proximal retention flange. In particular embodiments, the lock receiver is attached to the shunt portion. In particular embodiments, the lock receiver is attached to the distal retention flange.

Another feature of the present teachings provide a method of deploying an implantable medical device. In various embodiments, the device is delivered to an aperture. In some embodiments, the aperture is an existing one. In some embodiments, the aperture is created. In some embodiments, the device is delivered in its elongated configuration. In various embodiments, the device is delivered across the aperture. In various embodiments, the distal retention flange is released at one side of the aperture. In various embodiments, the proximal retention flange is released at the other side of the aperture. In various embodiments, the device transitions into its expanded configuration. This can be achieved by the device itself, for example, resuming a preformed expanded configuration because it is made of an elastic material, a super-elastic material, or a shape-memory alloy.

In various embodiments, the transition into the device's expanded configuration is achieved by using the constraint in the device. In some embodiments, the constraint is used to transition the device from its elongated configuration to its expanded configuration. In some embodiments, the constraint is used in combination with the device's resuming its preformed expanded configuration. In some embodiments, the constraint is used to maintain the device's expanded configuration. Thus, in certain embodiments, the mechanical property of the device, including the shunt portion, the distal retention flange, and/or the proximal retention flange, is changed.

Accordingly, in various embodiments, tension is applied to the axial constraining wire. As a result, in some embodiments, the shunt is transitioning to its expanded configuration. In some embodiments, when the clinician is satisfied with the delivery of the device, continuous application of tension results in the locking feature mating with the lock receiver. In some embodiments, the lock receiver captures the locking feature. In certain embodiments, the capture of the locking feature by the lock receiver is reversible. Thus, in particular embodiments, constraint can be removed and the device can be retrieved.

An aspect of the present teachings provide a method of removing an implantable medical device of the present teachings. In various embodiments, tension is applied to the proximal retention flange. In some embodiments, the proximal retention flange is retrieved into a catheter. In various embodiments, continuing application of tension pulls the shunt portion into the catheter. In various embodiments, continuing application of tension pulls the distal retention flange into the catheter. In various embodiments, retrieval of the catheter removes the device from the implantation site.

Another aspect of the present teachings provides a method of adjusting an implantable medical device of the present teachings at an implantation site. In various embodiments, after deploying a medical device of the present teachings as discussed herein, a clinician assesses whether the medical device is satisfactorily deployed. If, in some embodiments, the deployment is not satisfactory, the clinician uses a method of removing the device as discussed herein to retract the device into the deploying catheter. In some embodiments, the clinician redeploys the device. This process can be repeated until a satisfactory deployment is achieved. The assessment and/or removal can be conducted before or after the constraint is applied.

Figure 1:
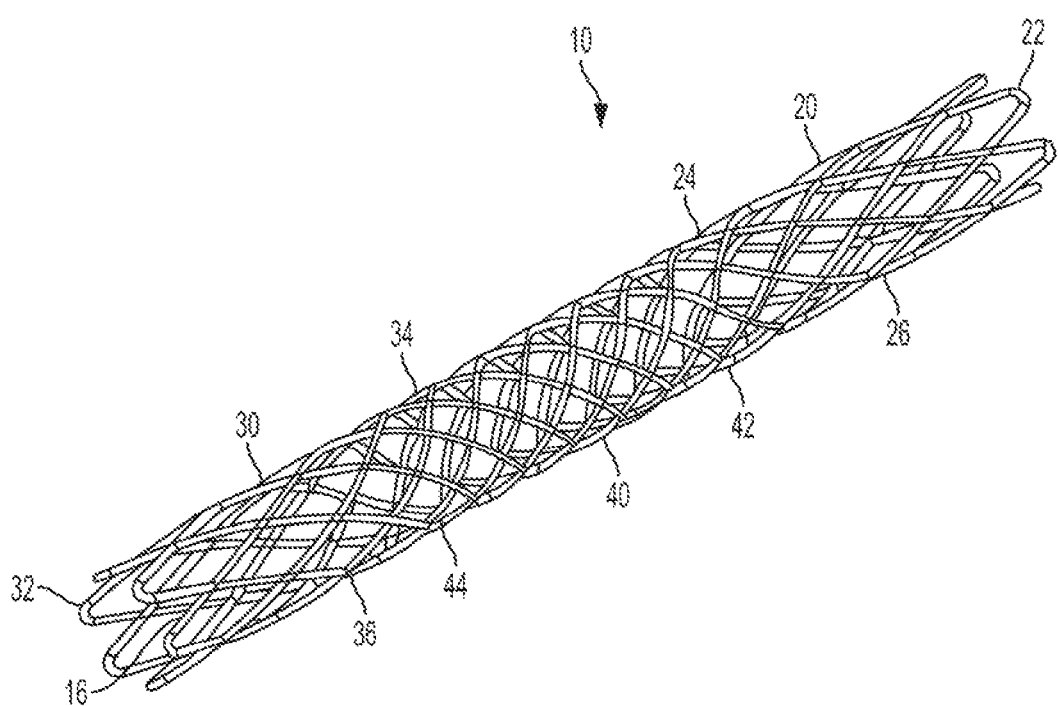
FIG. 1 is a perspective view of an exemplary medical device in accordance with some embodiments of the present teachings.
Figure 6:
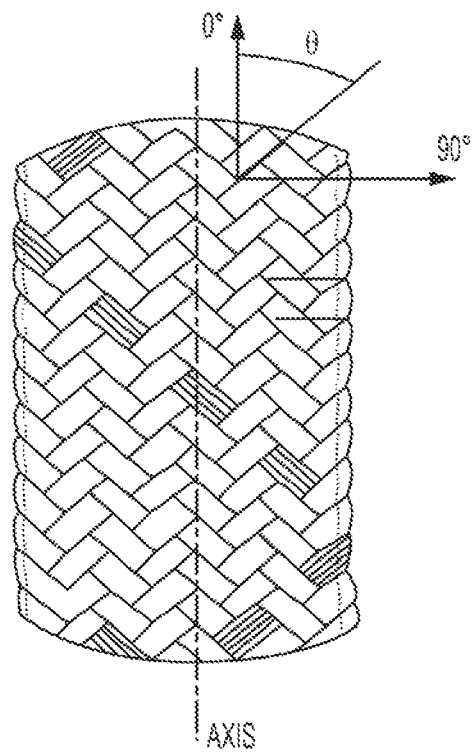
Figure 7:
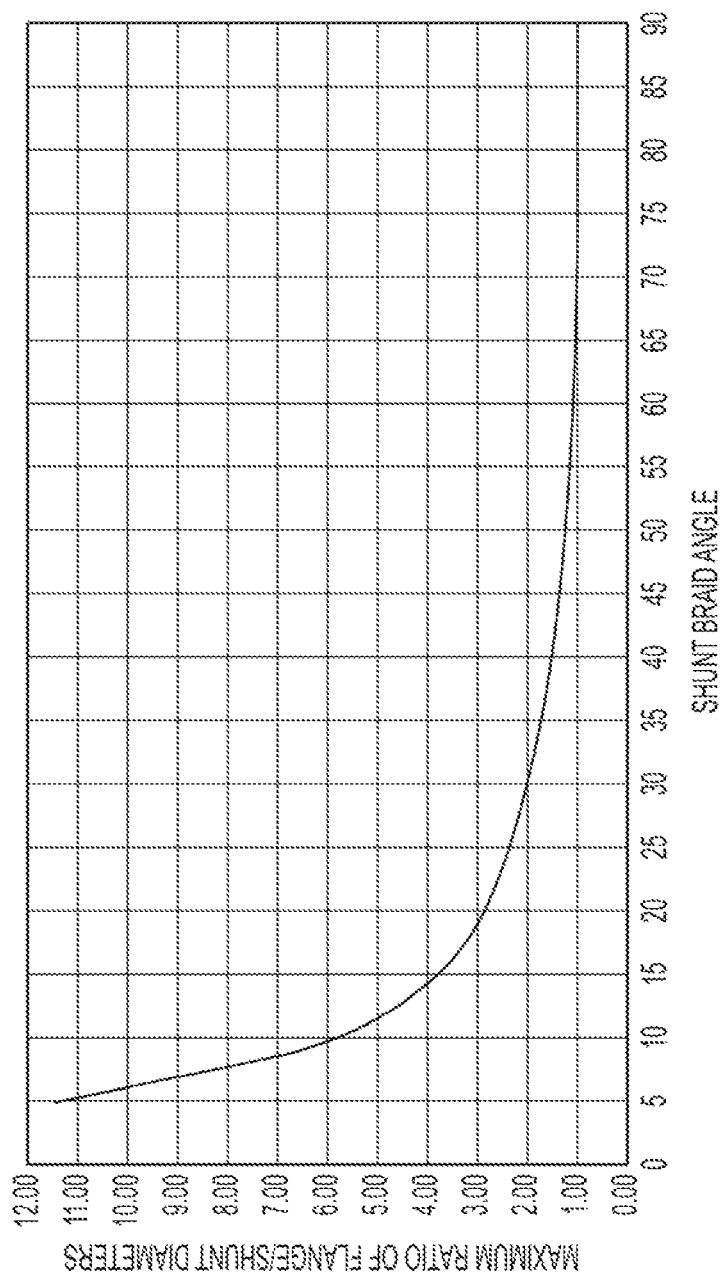
Figure 8:
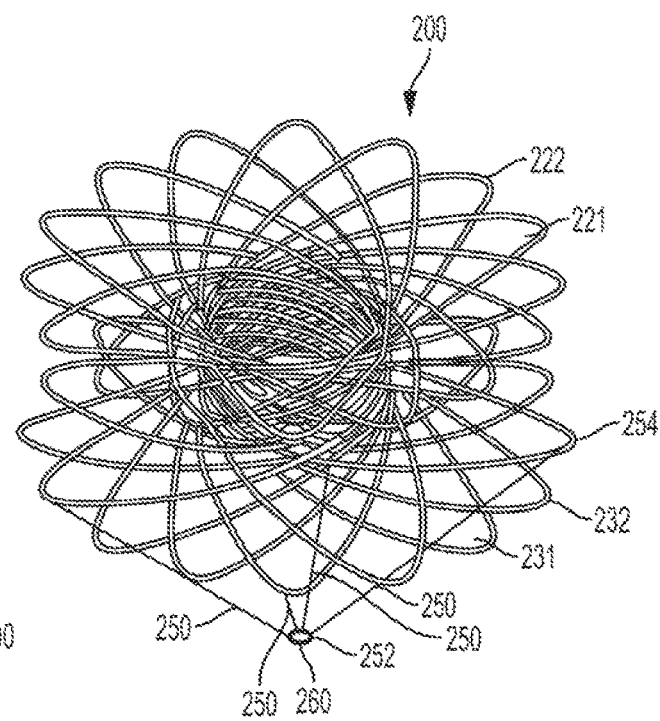
Figure 9:
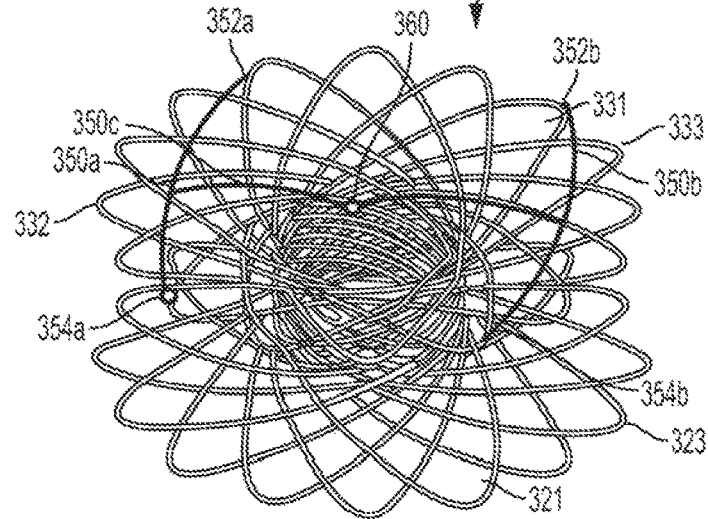
Figure 10:
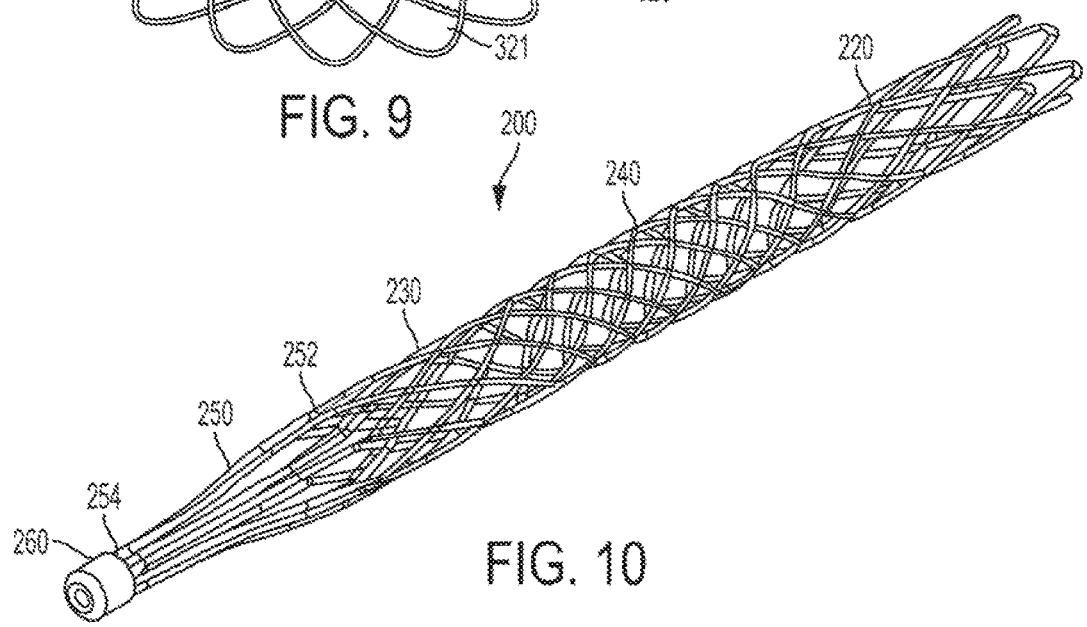
Figure 11:
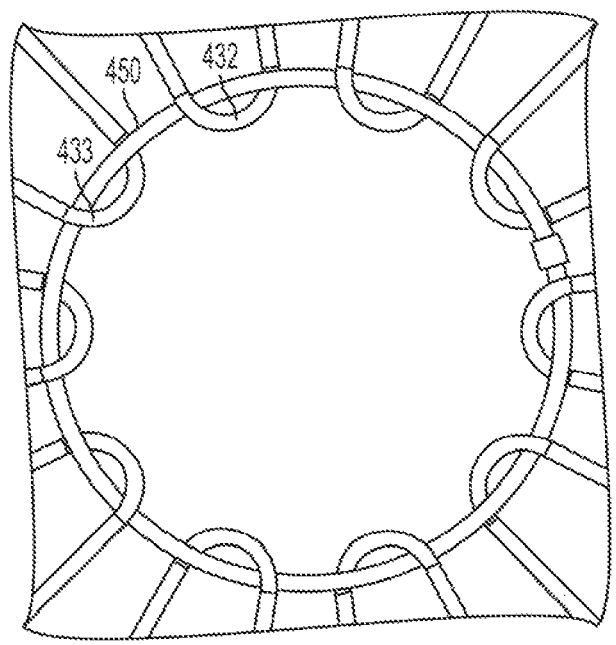
Figure 12:
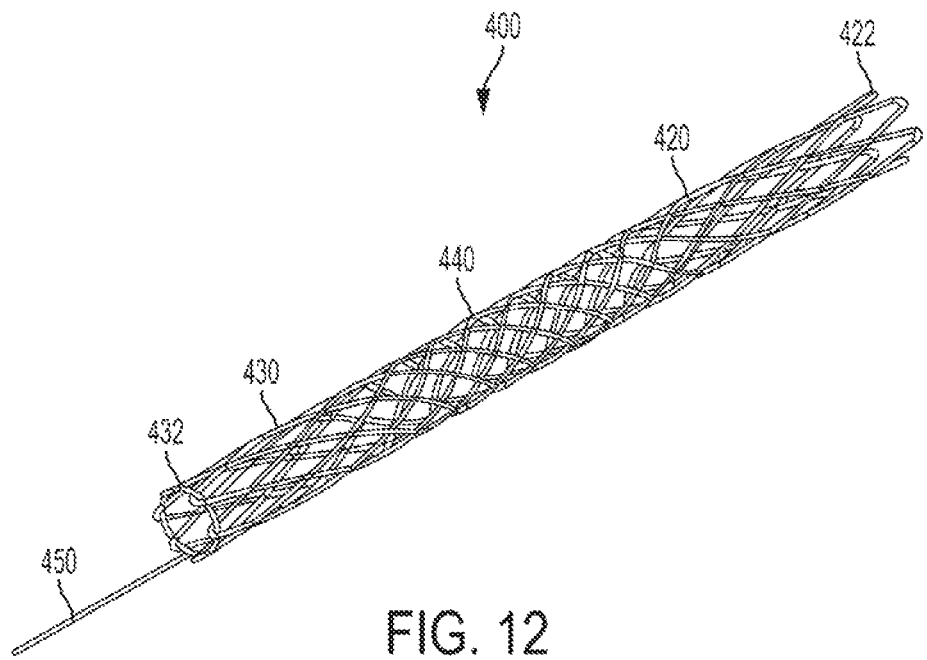
Figure 13:
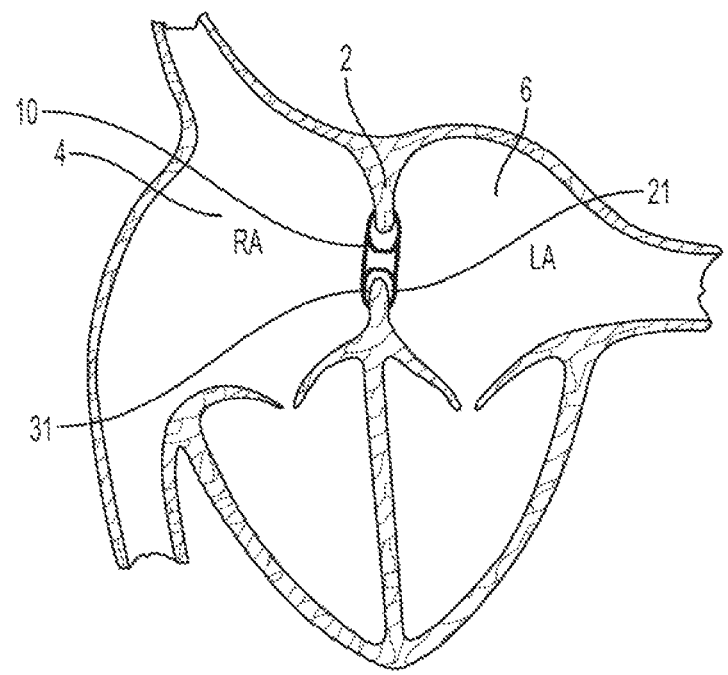
Figure 15:
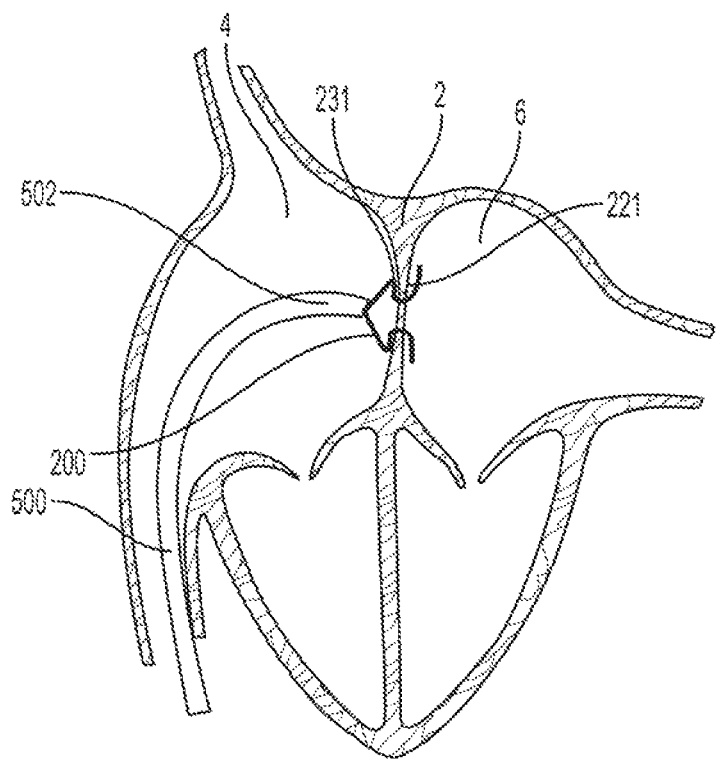
Figure 24:
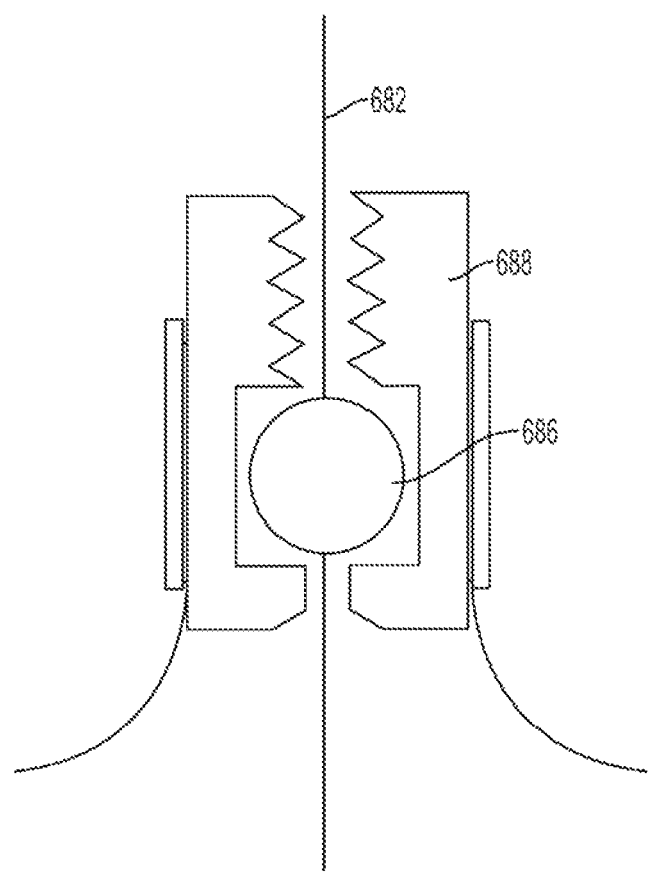

5a-5b are perspective views of an exemplary medical device of FIG. 1 in accordance with some embodiments of the present teachings;

FIG. 6 is exemplary view of a braided structure accordance with some embodiments of the present teachings;

FIG. 7 is an illustration of the relationship between a ratio of flange to shunt diameter versus braid angle of the shunt portion of an exemplary medical device in accordance with some embodiments of the present teachings;

FIG. 8 is a perspective view of an exemplary medical device in accordance with some embodiments of the present teachings;

FIG. 9 is a perspective view of an exemplary medical device in accordance with some embodiments of the present teachings;

FIG. 10 is a perspective view of the exemplary medical device of FIG. 8 in a constrained configuration;

FIG. 11 is a perspective view of an exemplary medical device in accordance with some embodiments of the present teachings;

FIG. 12 is a perspective view of the exemplary medical device of 11 in a constrained configuration;

FIG. 13 is a perspective view of the exemplary medical device of FIG. 1 deployed at a target site between left and right atrium of the heart in accordance with some embodiments of the present teachings;

FIGS. 14a-14e are perspective views demonstrating an exemplary process for deploying a medical device in accordance with some embodiments of the present teachings;

FIG. 15 is a perspective view of the exemplary medical device of FIG. 5 deployed at a target site between left and right atrium of the heart in accordance with some embodiments of the present teachings;

FIGS. 16a-16e are perspective views demonstrating an exemplary process for retrieving a medical device in accordance with some embodiments of the present teachings;

FIG. 17 is a perspective view of an exemplary device of the present teachings in its elongated configuration in accordance with some embodiments of the present teachings;

FIG. 18 is a perspective view of an exemplary device of the present teachings in its expanded configuration in accordance with some embodiments of the present teachings;

FIGS. 19a and 19b are perspective view of two exemplary devices of the present teachings in their respective expanded configurations viewing from their proximal sides in accordance with some embodiments of the preset teachings;

FIG. 20 is a perspective view of an exemplary device of the present teachings in its elongated configuration in accordance with some embodiments of the present teachings;

FIG. 21 is a perspective view of an exemplary device of the present teachings in its expanded configuration in accordance with some embodiments of the present teachings;

FIG. 22 is a perspective view of an exemplary device of the present teachings in its elongated configuration in accordance with some embodiments of the present teachings;

FIG. 23 is a perspective view of an exemplary device of the present teachings in its expanded configuration in accordance with some embodiments of the present teachings; and FIG. 24 is a perspective view of an exemplary constraint in accordance with some embodiments of the present teachings.

DETAILED DESCRIPTION

The present teachings are described more fully in connection with various embodiments. These embodiments are provided to illustrate various aspects of the present teachings, which can be embodied in many other forms, and, thus, the present teachings should not be construed as being limited to the embodiments set forth herein.

In addition, various drawings are provided herein to further illustrate various embodiments of the present teachings. Accordingly, these drawings and descriptions thereof, whether or not written in the context of "various embodiments," "some embodiments," "certain embodiments," "particular embodiments," "an embodiments," "another embodiment," "other embodiments," and the like, are for illustrative purpose and should not be construed to limit the scope of the present teachings or the enclosed claims. In certain instances, like numbers refer to like elements throughout.

The present teachings provide a medical device and methods of use thereof. For example, the medical device can be used to regulate the pressure in a heart chamber. Specifically, the medical device can be used to (a) change an elevated chamber pressure and/or (b) prevent embolization from the right to left atria in a patient who suffers from CHF or has a Patent Foramen Ovale (PRO) or an Atrial Septal Defect (ASD) but needs a residual flow between the atria so as not to traumatize the heart hemodynamics.

As used herein, the term "proximal" shall mean close to the operator (less into the body) and "distal" shall mean remote from the operator (further into the body). In positioning a medical device from a downstream access point, distal is more upstream and proximal is more downstream.

As used herein, the term "axial constraining wire" means a member which can take forms of a suture, cable, wire, or any other small diameter, flexible, semi-rigid or rigid material having a suitable tensile strength for the intended use. In addition, as used herein, the term "wire" can be a strand, a cord, a fiber, a yarn, a filament, a cable, a thread, or the like, and these terms may be used interchangeably.

The term "suture" used herein can be a strand, a wire, a cord, a fiber, a yarn, a filament, a cable, as thread, or the like, and these terms may be used interchangeably.

As explained, in further detail below, various embodiments of the present teachings provide medical devices for regulating the pressure in a heart chamber. In some embodiments, a medical device according to the present teachings includes a shunt portion. In some embodiments, the shunt portion is coupled with two retention flanges. In some embodiments, as medical device is positioned through an aperture in a septum. In particular embodiments, a medical device is used to create a shunt, for example, between the left and right atria. In some embodiments, the two retention flanges of the medical device, when deployed, are disposed on the opposite sides of the septum. In some embodiments, a medical device according to the present teachings transitions into an elongated profile for a percutaneous delivery and resumes its radially expanded profile in vivo after deployment. As used in this application, unless otherwise indicated, the term "aperture" refers to any anatomical anomalies such as PFO, ASD, VSD, or an anatomical feature created for the purpose of creating a shunt.

An embodiment of the device in the present teachings has a distal retention flange. In some embodiments, the distal retention flange is configured to be positioned at the left atrial side of the septum. An embodiment of the device includes a proximal retention flange. In some embodiments, the proximal retention flange is configured to be positioned at the right atrial side of the septum. An embodiment of the device includes a central shunt portion. In some embodiments, the central shunt portion is between of the distal and proximal flanges. In some embodiments, the central shunt portion is configured to create a conduit for blood to flow through. An embodiment of the device in the present teachings has an elongated profile for delivering through a catheter system. The elongated profile sometimes includes a delivery profile. An embodiment of the device in the present teachings has an expanded profile for securing the device across the septum. The expanded profile sometimes includes a deployed profile. In some embodiments, a device is configured to transits from its delivery profile to its deployed profile. In certain embodiments, this transition is through self-expansion. In certain embodiments, this transition is achieved with a mechanical actuation. During deployment, both distal and proximal retention portions of the device expand radially while contracts longitudinally. In other embodiments, the central shunt portion also expands radially while contracts longitudinally.

In some embodiments, the deployed distal and proximal portions have a general disc like profile which are configured to be positioned at each side of the atrial septum. In some embodiments, one or both of the deployed distal and proximal flanges are designed to be flanking away from the atrial septum. In another embodiments, one or both of the deployed distal and proximal flanges are configured to contact and/or compress against the atrial septum. In some embodiments, the device is secured to the treatment location across the atrial septum by one or both of the distal and proximal retention flanges. In another embodiment, the device is secured to the treatment location by the radial expansion of the central shunt portion of the device inside the aperture.

FIG. 1 illustrates an embodiment of the device (10) in an elongated delivery profile. One skilled in the art should appreciate that FIG. 1 illustrates the elongated configuration of the device without showing a catheter/sheath, which in various embodiment is used to deliver the device. As illustrated in FIG. 1, according to some embodiments, the device (10) is generally straightened and is suitable for being delivered via a delivery system (not shown). As illustrated in FIG. 1, both the distal and proximal portions (20, 30) of the device (10) are radially collapsed (or axially elongated or forming a generally tubular profile). Similarly, in the delivery configuration as seen in FIG. 1, the central shunt portion (40) also has a generally tubular profile. In some embodiments, the central shunt portion (40) of the device (10) is also axially elongated (or radially collapsed). In yet another embodiment, the central shunt portion (40) of the device (10) remains unchanged from its pre-set profile.

According to some embodiments, each distal and proximal portions (20, 30) of the device (10) has a free end (22, 32) and a fixed end (24, 34). In some embodiments, the free end (22) of the distal portion (20) forms a distal end (12) of the device (10). In some embodiments, the free end (32) of the proximal portion (30) forms a proximal end (14) of the device (10). In some embodiments, the central shunt portion (40) is between the distal and proximal portions (20, 30) of the device (10), with the fixed end (24) of the distal portion (20) connecting to a first end (42) of the central shunt portion (40) and the fixed end (34) of the proximal portion (30) connecting to a second end (44) of the central shunt portion (40).

Continuously referring, to FIG. 1, in this embodiment of the present teachings, the delivery profile of the device (10) is in a generally tubular profile. In various embodiments, the device includes a longitudinal lumen (16) running from the distal end (12) of the device to (10) the proximal end (14) of the device (10). In some embodiments, the longitudinal lumen runs through the elongated distal portion (20), the central shunt portion (40), and the proximal portion (30). According to some embodiments, a delivery catheter is (not shown) fitted inside the longitudinal lumen (16). This configuration can be used to facilitate a percutaneous delivery of the device (10) into a heart. In other embodiments, a delivery catheter engages the proximal end (14) of the device (10).

In some embodiments, the axial length of the device (10) in its delivery profile is 10-200 mm. In certain embodiments, the axial length of the device (10) in its delivery profile is 1-5 times of that in its deployed profile. In some embodiments, the overall cross sectional size of the device (10) in its delivery profile is 1-6 mm in diameter. In certain embodiments, the device is disposed in a 3-18 French-size catheter.

In some embodiments of the present teachings, in its delivery configuration, such as illustrated in FIG. 1, the shunt portion (40) of the device (10) has a generally uniform cross section with a diameter ranging from about 1 mm to about 10 mm. According to one embodiment of the present teachings, in the deployed configuration, the elongated distal and/or proximal portions (20, 30) also have a generally uniform cross section profile with a diameter ranging from about 1 mm to about 10 mm. In some embodiments, in this delivery configuration, the shunt portion (40) of the device (10) has a length of 1-50 mm. In some embodiments, the overall elongated device (10) has a length of 10-150 mm.

Although FIG. 1 illustrates that, according to some embodiments, in the delivery configuration, each of the shunt portion (40), the elongated distal portion (20), and the elongated proximal portion (30) of the device (10) has a generally uniform cross sectional profile, one ordinarily skilled in the art would understand that the cross sectional profile of each of the distal portion (20), the proximal portion (30), and the shunt portion (40) can be different from one another, and/or the cross sectional profile can vary from one part to another even within the same portion (e.g., the distal portion (20), the proximal portion (30), or the shunt portion (40)).

Figure 2:
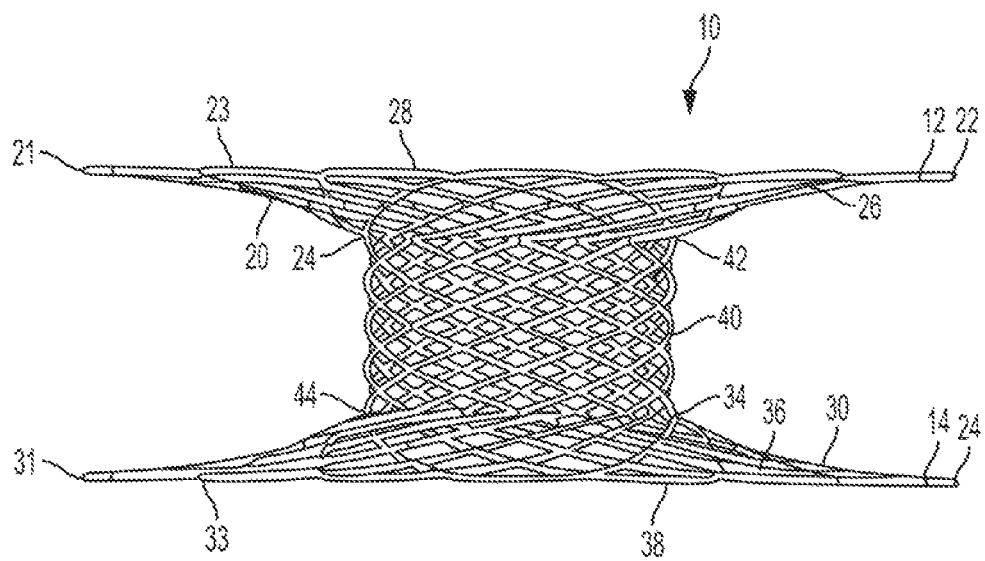
FIG. 2 is as perspective view of the exemplary medical device of FIG. 1 in a constrained configuration.

FIG. 2 illustrates one embodiment of the device (10) in present teaching in a radially expanded or deployed profile. As illustrated in FIG. 2, both the distal (20) and proximal (30) portions of the device (10) are radially extended (sometimes described as axially shortened or forming a generally disc shape) (21, 31). According to some embodiments, as the distal portion (20) of the device (10) transitions from its delivery profile to its deployed profile, the inner tubular surface (28) of the elongated distal portion (20) at the delivery profile transitions to form a surface of the distal retention flanges (21) facing away from the shunt portion (40) of the device, and facing away from the atrial septum when deployed at treatment location. According to some embodiments, as the proximal portion (30) of the device (10) transitions from its delivery profile to its deployed profile, the inner tubular surface (38) of the elongated proximal portion (30) at the delivery profile transitions to form a surface of the proximal retention flange (31) facing away from the shunt portion (40) of the device, and facing away from the atrial septum when deployed at treatment location. Accordingly, as the distal portion (20) of the device (10) transitions from its delivery profile to its deployed profile, the outer tubular surface (26) of the elongated distal portion (20) at the delivery profile transitions to form a surface of the distal retention flange (21) facing toward the shunt portion (40) of the device (10), and facing toward the atrial septum when deployed at treatment location. As the proximal portion (30) of the device (10) transitions from its delivery profile to its deployed profile, the outer tubular surface (36) of the elongated proximal portion (30) at the delivery profile transitions to form a surface of the proximal retention flange (31) facing toward the shunt portion (40) of the device (10), and facing toward the atrial septum when deployed at treatment location.

According to some embodiments, as the distal portion (20) of the device (10) transitions from its delivery profile to its deployed profile, the free end (22) of the distal portion (20) transitions radially outward to form the radial outward edge (23) of the distal flanges (21); and as the proximal portion (30) of the device (10) transitions from its delivery profile to its deployed profile, the free end (32) of the proximal portion (30) transitions radially outward to form the radial outward edge (33) of the proximal retention flange (31). As illustrated in FIG. 2, the distal retention flange (21) has a generally disc-like profile with the free end (22) of the distal portion (20) forming the radial outward edge (23) of the retention flange (21): and/or the proximal retention flange (31) has a generally disc-like profile with the free end (32) of the proximal portion (30) forming the radial outward edge (33) of the retention flange (31). In some embodiments, as the general diameters of the distal and proximal portions (20, 30) of the device (10) enlarge, the axial lengths of the distal and proximal portions (20, 30) reduce, and the axial distances between the free ends (22, 32) and fixed ends (24, 34) of the distal and proximal portions (20, 30) of the device (10) reduces, sometimes significantly, as illustrated.

Figure 3A:
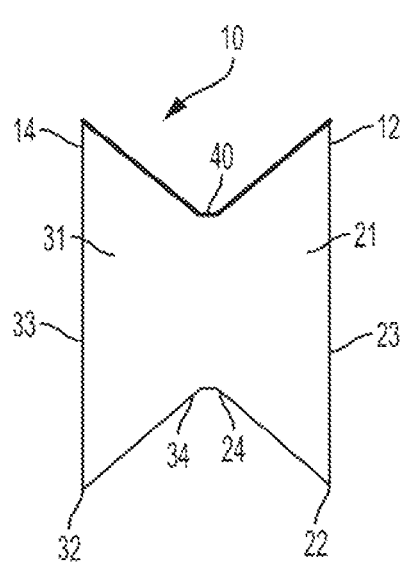
FIGS. 3a-3d are perspective views of an exemplary medical device of FIG. 1 in accordance with some embodiments of the present teachings.

According to some embodiments, in the deployed configuration, the free end (22) of the distal portion (20) remains distal to the fixed end (24) of the distal portion (20) of the device (10) as illustrated in FIG. 2 and/or FIG. 3a. According to some embodiments, the free end (32) of the proximal portion (30) remains proximal to the fixed end (34) of the proximal portion (30) of the device (10) as illustrated in FIG. 2 and/or FIG. 3a. Hence, when this embodiment of the device is deployed at a treatment location, the distal and/or proximal retention flanges (21, 31) flank away from the atrial septum with the radially outward edges (23, 33) of the retention flanges (21, 31) not contacting the atrial septum. Accordingly, in some embodiments, at least one of the distal and/or proximal retention flanges (21, 31) has a generally cone-shaped profile, a funnel-shaped profile, a hopper-like profile, and the like. One ordinarily skilled in the art would understand that other suitable profiles could also be used.

Figure 3B:
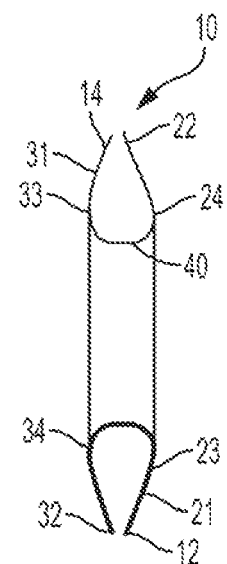

According to another embodiment, in the deployed configuration, the free end (22) of the distal portion (20) remains proximal to the fixed end (24) of the distal portion (20) of the device (10) as illustrated in FIG. 3b. According to another embodiment, the free end (32) of the proximal portion (30) remains distal to the fixed end (34) of the proximal portion (30) of the device (10) as illustrated in FIG. 3b. Consequently, when this embodiment of the device (10) is deployed at a treatment location, the radially outward edges (23, 33) of the retention flanges (21, 31) of the device (10) contact the atrial septum and provide additional securement to keep the device in place. Accordingly, in some embodiments, the distal and/or proximal retention flanges (21, 31) can have various profiles, including a generally straight slope profile, and a curved umbrella-shaped profile from the fixed ends (24, 34) to the free ends (22, 32). One ordinarily skilled in the art would understand that other suitable profiles could also be used.

Figure 3C:
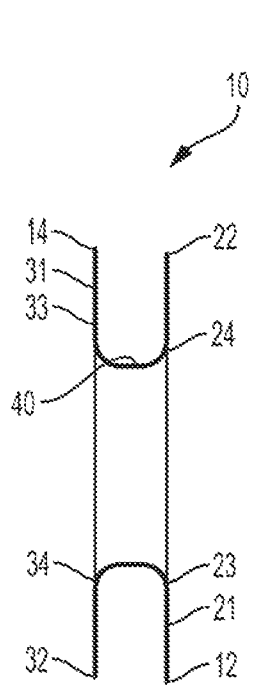
Figure 3D:
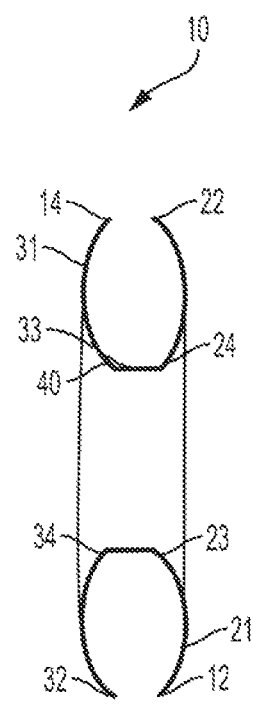

In another embodiment, in its deployed configuration, at least one of the free ends (22) of the distal and proximal portions (20, 30) remains substantially at the same axial location as the fixed ends (24, 34) of the corresponding distal portion or proximal portion (20, 30) of the device (10), as illustrated in FIG. 3c. In some embodiments, at least one of the distal retention flange (21) and the proximal retention flange (31) is relatively flat and in the shape of a disc, as illustrated in FIG. 3c. When deployed at a treatment location, a substantial part of the surface area of the retention discs (21, 31) contacts the atrial septum. In another embodiment, at least one of the distal retention flange (21) and the proximal retention flange (31) is in the shape of an umbrella with the flange surface doming away from the atrial septum when deployed at a treatment location. In some embodiments, at least one of the radially outward edges (23, 33) of the retention flanges (21, 31) of the device (10) contacts the atrial septum and provides additional support in keeping the device in place, as illustrated in FIG. 3d. One ordinarily skilled in the art would understand that distal and/proximal retention flanges (21, 31) can have other shapes or profiles.

According to some embodiments, where a deployed device has its free end (32) of the proximal portion (30) proximal to the fixed end (34) of the proximal portion (30) of the device (10), for example, as illustrated in FIG. 3a, the proximal retention flange of the device flanks away from the atrial septum. According to another embodiment, where a deployed device has its free end (32) of the proximal portion (30) distal to the fixed end (34) of the proximal portion (30) of the device (10), for example, as illustrated in FIG. 3b, the free end of the proximal portion of the device contacts the atrial septum. Yet in another embodiment, where a deployed device has its free end (32) of the proximal portion (30) remaining axially the same position as, while radially outward from, the fixed end (34) of the proximal portion (30) of the device (10), for example as illustrated in FIGS. 3c-3d, the free end (32) of the proximal portion (20) or/and a substantial surface area of the proximal retention flange (31) contacts the atrial septum.

One ordinarily skilled in the art would understand that each of the distal and proximal flanges (21, 31) can adopt any one of the configurations described above. In some embodiments, the distal and proximal retention flanges (21, 31) have a same shape and/or configuration, as illustrated in FIGS. 3a-3d. In another embodiment, the distal and proximal retention flanges (21, 31) have different shapes and configurations. Thus, the specific embodiment illustrated or/and described herein shall not be viewed as limiting.

Figure 4:
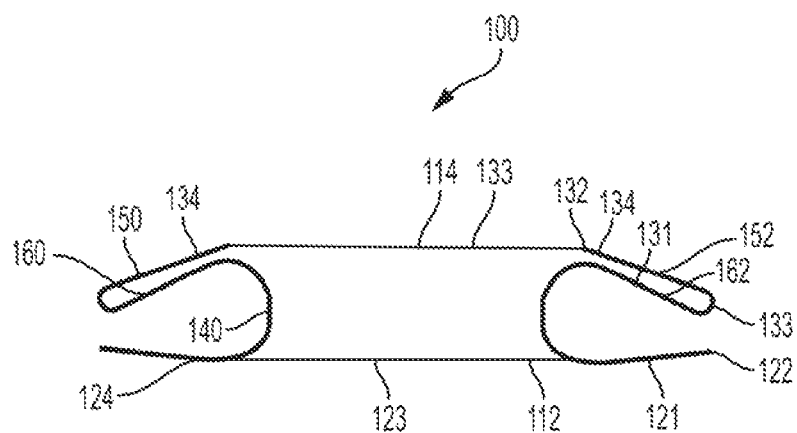
FIG. 4 is a perspective view of the exemplary medical device of FIG. 1 in accordance with some embodiments of the present teachings.

FIG. 4 illustrates another embodiment of the present teachings, where the proximal portion (130) of the device (100) expands and/or folds as the device transitions from delivery configuration to deployed configuration. According to some embodiments, as the proximal portion (130) of the device (10) transitions from its delivery profile to its deployed profile, the outer tubular surface of a first section (150) of the elongated proximal portion (130) in its delivery profile forms a first surface of (152) the device (100) In some embodiments, the first surface (152) faces away from the shunt portion (140) of the device (100) and away from the atrial septum when deployed at a treatment location. Accordingly, the outer tubular surface of a second section (160) of the elongated proximal portion (130) in its delivery profile forms a second surface (162) of the device (100). In some embodiments, the second surface (162) faces toward the shunt potion (140) of the device (100) and toward the atrial septum when deployed at treatment location. And the segment of the proximal portion (130) of the device (100) between the first and second sections (150, 160) of the elongated proximal portion of the device (100) forms a most radially outward edge (133) of the proximal retention flange (131) as shown in FIG. 4. As the proximal portion (130) of the device (100) transitions from its delivery profile to its deployed profile, in some embodiments, the general diameter of the proximal portion (130) of the device enlarges. As the proximal portion (130) of the device (100) transitions from its delivery profile to its deployed profile, in some embodiments, the axial length of the proximal portion (130) reduces. As the proximal portion (130) of the device (100) transitions from its delivery profile to its deployed profile, in some embodiments, the distance between the free end (132) and fixed end (134) of the proximal portion (130) of the device (100) reduces significantly as illustrated.

Figure 5A:
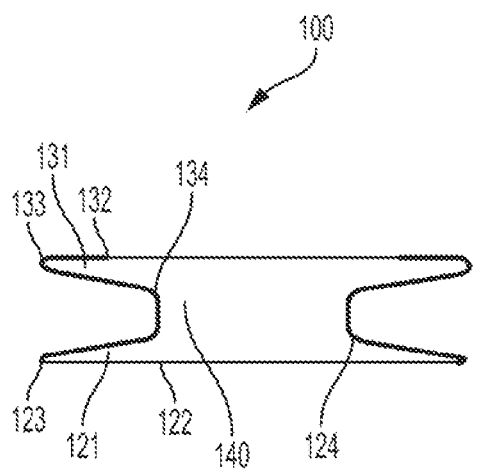

According to some embodiments of the present teachings, as illustrated in FIG. 5a, the radially outward edge (133) of the deployed proximal flange (131) is proximal to the fixed end (134) of the proximal portion (130) of the device (100). Consequently, when the device (100), in this particular embodiment, is deployed at a treatment location, the radially outward edge (133) of the proximal retention flange (130) flanks away from the atrial septum. In certain embodiments, the radially outward edge (133) of the retention flange (131) does not contact the atrial septum. Similar to what has been described herein, in some embodiments, the proximal retention flange (131) has a generally cone-shaped profile, a generally funnel-shaped profile, a generally hopper-like profile or the like.

In various embodiments of the present teaching, as illustrated in FIG. 4, the radially outward edge (133) of the deployed proximal flange (140) is distal to the fixed end (134) of the proximal portion (130) of the device (100). Consequently, when the device, in these particular embodiments, is deployed at a treatment location, the radially outward edge (133) of the proximal flange (131) contacts the atrial septum. In certain embodiments, the radially outward edge provides additional support to secure the device (100) at the treatment location. Similar to what has been described herein, in some embodiments, the proximal retention flange (131) has a generally straight-sloped profile, a curved umbrella-shaped profile (for example, from the fixed end (134) to the free end (132)), or the like.

Figure 5B:
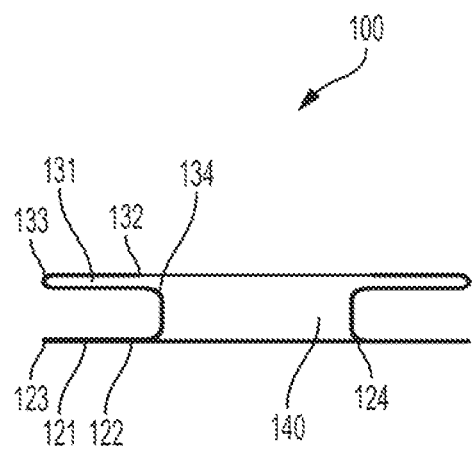

In yet other embodiments, as illustrated in FIG. 5b, the radially outward edge (133) of the proximal retention flange (131) remains axially at the same position as, while radially outward from, the fixed end (134) of the proximal portion (130) of the device (100). Similar to what has been described herein, in some embodiments, the proximal retention flange (131) is relatively flat and, in certain embodiments, in the shape of a disc, for example as illustrated in 5b. And when deployed at a treatment location, in some embodiments, a substantial surface area of the retention flange (131) contacts the atrial septum. In other embodiments, the proximal retention flange (131) has a shape of an umbrella with the flange surfaces doming away from the atrial septum when deployed at a treatment location. In certain embodiments, the radially outward edge (133) of the proximal retention flange (131) of the device (100) contacts the atrial septum. In certain embodiments, the radially outward edge (133) provides additional support to secure the device (100) at the treatment location.

One ordinarily skilled in the art would understand that although FIGS. 4-5 illustrate and disclose certain embodiments of the proximal retention flange (131), the illustration and disclosure can also apply to the distal retention flange (121) of the device (100). Additionally, the distal retention flange (121), the proximal retention flange (131), or both can incorporate any embodiments, described herein and/or illustrated in FIGS. 2-5. And in some embodiments, the proximal and distal retention flanges (121, 131) have a same shape or/and profile. In other embodiments, the proximal and distal flanges (121, 131) have different shapes or/and profiles.

According to some embodiments, the radial span of the distal and proximal retention flanges (21, 31, 121, 131) is minimized as much as possible in the device. In some embodiments, the distal and proximal retention flanges (21, 31, 121, 131) have a same size. In other embodiments, a distal retention flange (21, 121) is slightly larger than a proximal retention flange (31, 131). This can be used to account for the typical left-to-right trans-atrial pressure gradient or/and to facilitate deployment. In some embodiments, a distal retention flange (21, 121) has a diameter of 8-40 mm upon deployment. In other embodiments, a proximal retention flanges (31, 131) has a diameter of 7-38 mm upon deployment.

One skilled in the art would understand that distal and proximal flanges (21, 31, 121, 131) of various sizes, shapes, or/and profiles can be combined to accomplish the goal of securing the device (10, 100) in a treatment location, as well as lowering the risk of the device impinging on adjacent cardiac structures.

In some embodiments, when deployed at a treatment location, the distal and proximal retention flanges (21, 31, 121, 131) are configured to apply compression force against the respective sides of the atrial septum either along their radially outer edges (23, 33, 123, 133) or throughout the entire flange surface. In some embodiments, when deployed at a treatment location, the distal and proximal retention flanges (21, 31, 121, 131) are configured to be in contact with the respective sides of the atrial septum. In certain embodiments, when deployed at a treatment location, the distal and proximal retention flanges (21, 31, 121, 131) are configured not to compress the respective sides of the atrial septum. In some embodiments, when deployed at a treatment location, the distal and proximal retention flanges (21, 31, 121, 131) are configured not to be in contact with the atrial septum.

Referring back to FIG. 2, according to some embodiments, the shunt portion (40, 140) between the distal and proximal retention flanges (21, 31, 121, 131) also has a generally tubular shape in its deployed configuration. In some embodiments, the shunt portion (40, 140) radially expands during deployment. In some embodiments, the shunt portion (40, 140) axially contracts during deployment. Alternatively, the shunt portion (40, 140) remains unchanged geometrically during deployment. According to some embodiments, the shunt portion (40, 140) of the device (10, 100) is configured to be positioned through an aperture across the atrial septum. In some embodiments, upon deployment, the shunt portion (40, 140) is configured to be larger than the size of the aperture. In certain embodiments, upon deployment, the shunt portion (40, 140) applies a compression force along its outside tubular surface toward the surrounding tissues. Doing so, in certain embodiments, the device (10, 100) is secured at the treatment location. In another embodiment, upon deployment, the shunt portion (40, 140) has a same size as or is slightly smaller than the size of the aperture. When deployed inside the aperture, the shunt portion (40, 140) contacts, without applying additional forces to, the surrounding tissues.

In some embodiments of the present teachings, when the device ((10, 100) is fully deployed, the cross section of the shunt portion (40, 140) has a diameter ranging from about 5 mm to about 30 mm. In some embodiments, the distal and/or proximal retention flanges (21, 31, 121, 131) have a diameter ranging from about 7 mm to about 40 mm. In some embodiments, when the device (10, 100) is fully deployed, the length of the shunt portion (40, 140) of a deployed device ranges from about 1 mm to about 30 mm. In some embodiments, the overall length of a deployed device, including the distal, shunt, and proximal portions, ranges from about 1 mm to about 40 mm.

According to one embodiment of the present teachings, the shunt portion (40, 140) has a generally tubular shape. In some embodiments, a cross section of the shunt portion (40, 140) of the device is circular or polygonal. In certain embodiments, a cross section of the shunt portion (40, 140) of the device is square or hexagonal.

Another aspect of the present teachings provides an atrial shunt device (10, 100) with a braided structure. Referring to FIGS. 1 and 2, the device has a generally braided structure, produced by intertwining a plurality of strands diagonally such that a group of the strands pass alternately over and under another group of strands in the opposite direction. As one skilled in the art would understand, in a braiding operation, the strands are braided over a mandrel. In general, the mandrel is not rotated, while the strand carriers, which are mounted on a wheel normally to the mandrel axis, rotate around the mandrel axis.

According to some embodiments, braiding patterns that can be used in constructing a device of the present teachings include various commonly used interlacing patterns, such as plain, twill, panama weave, etc. One skilled in the art would understand that a braiding pattern influences the order of interlacing points in the braided. Accordingly, various braid patterns provide different mechanical properties for the corresponding braided structures.

In some embodiments, the strands are laser welded at certain locations. In certain embodiments, this is done for the shape-forming purpose. In some embodiments, the strands are laser welded at certain intersections. In certain embodiments, strands at some of the intersections at the shunt portion (40, 140) of the device (10, 100) are laser welded. Welding at such intersections sometimes increases the stiffness of the shunt portion (40, 140). In certain embodiments, strands at some of the intersections within the shunt portion (40, 140) of the device (10, 100) are laser welded. In particular embodiments, welding at such intersections provides the shunt portion (40, 140) with greater stiffness.

According to some embodiments of the present teachings, a braid angle "θ" is defined, as illustrated in FIG. 6, as half of the angle of the interlacing between the two nonparallel sets of strands in a braid. Sometimes, a braid angle "θ" is also defined as the angle between a strand of wire and the machine axis. By adjusting the braid, angle "θ," the hoop and longitudinal stiffness can be optimized. One skilled in the art would understand that the greater is the braid angle "θ," the greater will be the hoop strength.

According to some embodiments of the present teachings, the braid angle "θ" of the device varies at various portions of the device. According to some embodiments, such as one illustrated in FIG. 2, the proximal retention flange (31, 131) of a fully deployed device (10, 100) has a first braid angle. In some embodiments, the fully deployed shunt portion (40, 140) of a device (10, 100) has a second braid angle. In some embodiments, the distal retention flange (21, 121) of a fully deployed device (10, 100) has a third braid angle. In some embodiments, the second braid angle is greater than the first braid angle or/and the third braid angle. In other embodiments, the second braid angle is smaller than the first braid angle or/and the third braid angle. In some embodiments, the first and third braid angles are the same. In some embodiments, the first and third braid angles are different. According to some embodiments of the present teachings, the braid angle at the shunt portion (40, 140) of the device (10, 100) is greater than 30 degrees.

FIG. 7 illustrates a relationship between the ratios of a flange diameter to a shunt diameter in a device v. the braid angles of the shunt portion (40, 140) of the device. The curved line on the graph is defined as $$1/\sin \theta$$

wherein 1 represents the nominal shunt diameter and θ represents the braid angle of the shunt portion (40, 140). According to some embodiments, the ratio of flange/shunt diameter remains on or above the curve in FIG. 7. That is, the ratio of flange/shunt diameter equals or greater than 1/sin θ. For example, in some embodiments, as the device deploys at a treatment location, the shunt portion (40, 140) assumes a braid angle of 60 degree and the diameter of the distal and/or proximal flange (21, 121, 31, 131) is at least 1.2 times of that of the shunt portion (40, 140).

According to some embodiments, the shunt portion (40, 140) of a deployed device (10, 100) is configured to have a greater hoop stiffness than the distal or/and proximal retention flanges (21, 121, 31, 131) of the deployed device (10, 100) is. In some embodiments, the shunt portion (40, 140) of a deployed device (10, 100) has a similar hoop stiffness as the distal or/and proximal retention flanges (21, 121, 31, 131) of the deployed device (10, 100). In some embodiments, when the device (10, 100) is deployed at a treatment location, as the shunt portion (40, 140) of the device (10, 100) resumes its pre-set deployed configuration, the shunt portion (40, 140) of the device (10, 100) gains a greater hoop stiffness so that it pushes tissues at the aperture radially outwardly and enlarges the opening without the need of a prior dilation of the aperture before deploying the device (10, 100). In some embodiments, a greater hoop stiffness of the shunt portion (40, 140) of the device (10, 100) is also important for maintaining a more consistent shunt sizing regardless of the anatomic character or/and in-growth of atrial septum tissues.

As known to those skilled in the art, the braid angle changes as the device (10, 100) transitions from its elongated (delivery) profile to its expanded (deployed) profile. According to some embodiments, the braid angle in the distal portion (20, 120) of the device (10, 100) increases as said portion of the device (10, 100) expands radially and contracts longitudinally. Similarly, the braid angle in the proximal portion (30, 130) of the device (10, 100) increases as said portion of the device (10, 100) expands radially and contracts longitudinally. According to some embodiments, as the shunt portion (40, 140) of the device (10, 100) expands radially and contracts longitudinally, the braid angle of the shunt portion (40, 140) also increases. In an alternative embodiment, the shunt portion (40, 140) of the device (10, 100) remains the same from the delivery profile to the deployed profile. In certain embodiments, the braid angle of the shunt portion (40, 140) remains constant during the deployment.

According to some embodiments, as the device (10, 100) transitions from its delivery profile to its deployed profile, the braid angle of each of the distal portion (20, 120), the shunt portion (40, 140), and the proximal portion (30, 130) of the device (10, 100) increases. In certain embodiments, as the distal portion (20, 120), shunt portion (40, 140) and/or proximal portion (30, 130) contracts longitudinally and expands radially, the braid angle of each of the distal, shunt, and proximal portions increases. As the distal portion (20, 120), shunt portion (40, 140) and/or proximal portion (30, 130) reaches its fully deployed configuration, the braid angle of each of these portions reaches their pre-set maximum value.

According to some embodiments of the present teachings, at least one of the braid angles of the distal portion (20, 120), shunt portion (40, 140), and proximal portion (30, 130) changes from 2 to 80 degrees as the device (10, 100) transitions from its elongated delivery profile to its expanded deployed profile. In some embodiments, the extents of the braid angle changes during the delivery-to-deployed profile transition are the same for each portion of the device (10, 100). In some embodiments, the extents of the braid angles changes during the delivery-to-deployed profile transition are different for one portion of the device (10, 100) to another. In some embodiments, the extent of the braid angle change for the distal portion (20, 120) is greater than that of the braid angle change for the shunt portion (40, 140). In yet other embodiments, the extent of the braid angle change for the distal portion (20, 120) is lesser than that of the braid angle change for the shunt portion (40, 140). In some embodiments, the extent of the braid angle change for the proximal portion (30, 130) is greater than that of the braid angle change for the shunt portion (40, 140). In yet other embodiments, the extent of the braid angle change for the proximal portion (30, 130) is lesser than that of the braid angle change for the shunt portion (40, 140).

One skilled in the art would know that the braid angle is controlled by adjusting the number of carriers, the speed in which the carrier travels, and the feed rate of the mandrel through the braider. One skilled in the art would understand that the braid angle change can also be achieved by braiding strands on a shaped mandrel. Additionally, strands can be bent in order to achieve acute changes in the braid angle, for example, at places where the distal portion (20, 120) changes into the shunt portion (40, 140) of the device, or the place where the proximal portion (30, 130) changes into shunt portion (40, 140) of the device (10, 100).

As those skilled in the art would know, the term "braid strand density" is often described as picks per inch (PPI), which is the number of strand crossovers per inch of shaft. In many instances, a braid strand density determines the mesh site for a deployed device (10, 100). According to some embodiments, the braid strand density for a device of the present teachings is 10-120 PPI during a braiding process. As the device (10, 100) deploys in vivo, according to some embodiments, both the distal and proximal flanges (21, 121, 31, 131) form open mesh-like surface structures. The open mesh-like surface structure does not impede blood from flowing through the device (10, 100) or/and the aperture. Thus, the higher is the braid strand density, the smaller will be the mesh structure. According to some embodiments, each mesh opening has a cross-sectional area from about 1 mm$^2$ to about 5 mm$^2$. According to some embodiments, the accumulated area of the openings in the mesh-like surface structure on the entire device (10, 100) is about 50-95% of the entire surface area of the device (10, 100).

According to some embodiments, the distal and/or proximal retention flanges (21, 121, 31, 131) have a uniform braid angle throughout its/their planary surface. According to some embodiments, the distal and/or proximal retention flanges (21, 121, 31, 131) have a uniform braid wire density throughout its/their planary surface. According to some embodiments, the distal and/or proximal retention flanges (21, 121, 31, 131) have an open mesh-like surface structure with a generally uniform size throughout its/their planary surface.

One skilled in the art would understand that the braid angle or/and braid wire density can vary throughout its/their planary surface to satisfy various purposes of the application. For example, the braid wire density can be less toward the free end (22, 122, 32, 132) of the distal/proximal retention flange (21, 121, 31, 131) and more toward the other end of the flange. As a result, in some embodiments, the free end (22, 122, 32, 132) of the flanges (21, 121, 31, 131) is more flexible and conforms more readily to the anatomy of the surrounding tissues. Additionally, a greater braid wire density leads to a smaller sized mesh-like surface structure which, in turn, prevents tissue in-growth and allows the shunt to stay open over a greater time. And as smaller braid wire density leads to a larger sized mesh-like surface structure which, in turn, allows tissue in-growth over the structure and secures the implant in place. In some embodiments, the braid angle is smaller at the free end (22, 122, 32, 132) of the retention flange (21, 121, 31, 131) and greater at the other end of the flange (21, 121, 31, 131). Accordingly, a portion of the distal/proximal retention flanges (21, 121, 31, 131) has a stronger hoop strengths than other portion. One skilled in the art would recognize that the size, shape, braid angle, or/and braid wire density of the distal and proximal retention flanges (21, 121, 31, 131) can vary along the surface of these portions.

In some embodiments, the shunt portion (40, 140) of the device (10, 100) has a uniform braid angle throughout its tubular surface. In some embodiments, the shunt portion (40, 140) of the device (10, 100) has a uniform braid wire density throughout its tubular surface. In some embodiments, the shunt portion (40, 140) of the device (10, 100) has a mesh-like surface structure with a generally uniform size. Similar to what's has been described here, the braid angle and braid wire density can vary, for example, to satisfy various purposes. One skilled in the art would recognize that the size, shape, braid angle, or/and braid wire density of the shunt portion (40, 140) of the device (10, 100) can vary along the surface of shunt portion (40, 140).

According to some embodiments, the device (10, 100) is manufactured by braiding the distal, shunt, and proximal portions (20, 120, 40, 140, 30, 130) together as a unity. In an alternative embodiment, the device is manufactured by braiding the distal, shunt, and proximal portions (20, 120, 40, 140, 30, 130) separately and joining the portions together after braiding.

According to some embodiments, at least one of the distal and proximal retention flanges (21, 121, 31, 131) and shunt portion (40, 140) is made of a biocompatible metal or polymer. In various embodiments, the entire device (10, 100) is made of a biocompatible metal or polymer. In some embodiments, the device (10, 100) in its entirely or the portion(s) with curved/bent deployment configuration is made of an elastic material, a super-elastic material, or a shape-memory alloy which allows the above portions to be distorted into a generally straightened profile during the delivery process and resume and maintain its intended profile in vivo after it is deployed from a delivery catheter. In some embodiments, the device (10, 100) is made of stainless steel, nitinol, Titanium, Elgiloy, Vitalium, Mobilium, Ticonium, Platinore, Stellite, Tantalum, Platium, Hastelloy, CoCrNi alloys (e.g., trade name Phynox), MP35N, CoCrMo alloys, any other metallic alloys, or a mixture thereof. Alternatively, in such embodiments, a part of the device (10, 100) or the entire device is made of a polymer, such as PTFE, UHMPE, HDPE, polypropylene, polysulfone, or other biocompatible plastic. The surface finish of the device (10, 100) can be textured to induce tissue response and tissue in-growth for improved stabilization. Alternatively, a part of or all the device (10, 100) can be fabricated from a resorbable polymer such as polyactic acid, polyglycolic acid, polycaprolactone, a combination of two or more of the above or a variety of other resorbable polymers that are well known to those skilled in the art.

According to some embodiment, the device (10, 100) is constructed from metallic strands. The term "strand" used herein can be wires, cords, fibers, yarns, filaments, cables, threads, or the like, and these terms may be used interchangeably. According to one embodiment, the wire used to form the device (10, 100) has a general diameter from about 0.02 mm to about 1 mm.

In some embodiments, a braided device (10, 100) of the present teachings includes 6-48 wires. In another embodiment, the braided device (10, 100) includes 3-24 folded wires as starting at one end of the device (10, 100) and braiding toward the other end of the device. Each end of the folded strand is braided in the opposite helical directions. In another embodiment, the braided device (10, 100) is formed from a single strand that is helically wound from one end of the device (10, 100) to the other end of the device (10, 100). Upon reaching to the end of the device (10, 100), the strand is bent and wound in the opposite helical direction while passing alternately over and under the previously formed helical windings to form a braided structure. The number of passes of the strand from one end of the device (10, 100) to the other may be adjusted in conjunction with the braid angle to form a desired strand mesh density. One skilled in the art would understand that more or less wires can be used to form the braid structure of the device (10, 100).

In yet another embodiment, the ends of the strands are bent, braided, or otherwise tugged back toward the opposite end of the device (10, 100) and into the braid intersections so that the braided structure does not unwind itself. According to some embodiments, at least some of the loose ends of the wire are optionally laser welded, crimped, or constrained by a sleeve to the adjacent wire.

In one embodiment, the device (10, 100) is braided from strands each of which has a diameter that varies along its length. In one embodiment, a strand with a varying diameter is used such that the shunt portion (40, 140) of the device (10, 100) is braided with a section of the strand that has a larger diameter while the distal and proximal flanges (21, 121, 31, 131) are braided with sections of the same strands that have smaller diameters. This provides a device (10, 100) with a sufficiently stiff central shunt (40, 140) and relatively flexible (compliant) distal and proximal flanges (21, 121, 31, 131). Strands of varying diameter may be formed by a variable drawing process. Various combinations of diameter may be used along the length of the strand to impart sufficient stiffness and compliance where it is needed.

According to one embodiment of the present teachings, the device (10, 100) is braided into a tubular form and then shaped to its final configuration. In one embodiment, if a sufficiently elastic and resilient material such as nitinol is used, the structure is preformed into the finished shape and then elastically deformed and stowed for the delivery. In various embodiments, after deployment, the device (10, 100) elastically recovers to its pre-formed shape. In some embodiments, the shunt portion (40, 140), the distal portion (20, 120), or/and the proximal portion (30, 130) are manually expanded to desired diameters. In some embodiments, the shunt portion (40, 140), the distal portion (20, 120), or/and the proximal portion (30, 130) is/are curved to a pre-set shape and heat set in an oven while constrained to the desired shape. According to some embodiments, heat setting is incorporated before, during, or after the wire is braided on the mandrel. In certain embodiments, the pre-setting or/and heat setting can be used to control the superelasticity of the nitinol wire and set the final shape of the device (10, 100), including the size and shape of the two retention disks and the outer diameter of the shunt portion (40, 140) of the device (10, 100).

FIGS. 8-9 illustrate an exemplary retrievable atrial shunt device (200, 300) in its deployed configuration. Similar to embodiments described herein in relationship to FIGS. 1-5, as illustrated in FIG. 8, the exemplary atrial shunt device (200) has a distal retention flange (221), a proximal retention flange (231), and a shunt potion (240). The distal retention flange (221), proximal retention flange (231), and shunt portion (240) of the exemplary atrial shunt device (200) are made of a braided structure. In addition, the proximal retention flange (231) is configured to form a releasable attachment between the atrial shunt device (200) and a delivery system in such way that device (200) can be reposition and retrieved.

Now referring to FIG. 8, the exemplary atrial shunt device (200) includes a plurality of proximal struts (250). Each proximal strut (250) has one end (252) connecting to the free end (232) of the proximal flange (231) and a second end (254) connecting to the second ends of other proximal struts to form a proximal hub (260). In one embodiment, the proximal hub (260) is configured to releasably connect the device to a delivery catheter. Although FIG. 8 illustrates four proximal struts (250), one skilled in the art would understand that so long as the proximal struts (250) do not impede blood flow through the shunt device (200), the number of proximal struts (250) can be any number between two and ten without any significant changes to the device or methods of making or using thereof described herein.

In some embodiments, for example, as illustrated in FIG. 8, all proximal struts (250) of the device (200) join one another to form a proximal hub (260). In other embodiments, for example, as illustrated in FIG. 9, a first proximal strut (350a) has a first end (352) connecting to a first place on the free end (352a) of the proximal retention flange (331) and a second end (354) connecting to a second place on the free end (332) of the proximal retention flange (331); a second proximal strut (350b) has a third end connecting to a third place on the free end (332) of the proximal retention flange (331) and a fourth end connecting to a fourth place on the free end (332) of the proximal retention flange (331); and a third proximal strut (350c) connects the first (350a) and second proximal strut (350b). According to some embodiments of the present teachings, the third proximal strut (350c) is also configured to be connected with a delivery mechanism, for example, by incorporating a proximal hub (360) or by direct attachment. One skilled in the art would understand that more than three proximal struts (350a, 350b, 350c) can be used to create a similar design so long as the proximal hub (360) does not impede blood flow.

In some embodiments, each of the proximal struts (250, 350) is the same size as the braided strand. In other embodiments, the proximal strut (250, 350) has a different size from the braided strand. In some embodiments, the proximal struts (250, 350) are a same size. In other embodiments, at least one of the struts (250, 350) has a size different from at least another proximal struts.

Referring to FIGS. 8 and 9, the exemplary proximal hub (260, 360) in these examples is a circular ring that connects to all of the proximal struts via an end of each of the proximal strut. One skilled in the art would understand the proximal hub (260, 360) of the device (200, 300) is configured to connect with a delivery catheter. Thus, the specific design of the proximal hub (260, 360) can be anything known to those in the field and suitable for connecting to the distal end of a delivery catheter/sheath. For example, in one embodiment, the proximal hub (260, 360) has a thread feature which is configured to be threadably connected to a delivery catheter. In another example, the proximal hub (260, 360) is configured to join the distal end of a delivery catheter in a pin-through-hole mechanism, a ball-claw mechanism, a groove-collet mechanism, or any other type of interlocking connection. One skilled in the art would understand that a variety of connection mechanisms can be used between the proximal hub (260, 360) and the delivery catheter.

FIGS. 8-9 illustrate various exemplary retrievable/repositionable atrial shunt devices (200, 300) in their deployed configurations. In one embodiment, as illustrated in FIGS. 8-9, the proximal strut (250, 350) extends proximally from the proximal retention flange (231, 331) and forms a general cone shape. When the device is deployed at a treatment location, the proximal struts (250, 350) extend into the right atrium. In other embodiments, the proximal struts (250, 350) are aligned in the same plane as the proximal retention flange (231, 331). In such embodiments, the device (200, 300) has a generally small profile. In some embodiments, the deployed proximal struts (250, 350) also form a filter or flow control element that prevents blood clog from entering the left atrium through the shunt.

FIG. 10 illustrates another embodiment of the present teachings where the retrievable/reposition atrial shunt device (200) is in its elongated delivery profile. Specifically, the distal retention flange (221) collapses radially and extends axially to form an elongated distal portion (220) and the proximal retention flange (231) collapses radially and extends axially to form an elongated proximal portion (230). In some embodiments, the shunt portion (240) of the device (200) also collapses radially and extends axially to form an elongated shunt portion (240). In another embodiment, the shunt portion (240) of the device remains the same at the delivery and deployed configurations. Continuing referring to FIG. 10, the proximal struts (250) of the device also collapses radially as the first ends (252) of the proximal struts (250) connect with the elongated proximal portion (230) of the device (200) and extend axially and the second ends (254) attaches to a proximal hub (260), which is configured to attach to the distal end of a delivery catheter (not shown).

FIG. 11 illustrates a prospective view of another embodiment of a retrievable/repositionable device (400) of the present teachings. Instead of proximal struts connecting at one end to the proximal retention flange and at the other end to a proximal hub, which is configured to engage the distal end of a delivery catheter, a strand loop (450) extends through braided strands (433) at the free end (432) of the proximal portion (430) of a device (400). According to some embodiments, this strand loop (450) threads through all meshes at the free end (432) of the proximal portion (430) of the device (400) and each of the braided mesh is slidable along the strand loop (450). The loop strand (450) is configured to accommodate the size of the free end (432) of the proximal flange (431) at its fully deployed configuration. Thus, for an embodiment where the free end (32) of the proximal portion (30) forms a radially outward edge (33) of the proximal retention flange (31), such as shown in FIG. 2, the loop stand (450) has a relatively great size. And for an embodiment where the radially outward edge (33) of the proximal retention flange (31) is a segment of the proximal portion (30) of the device (10), such as shown in FIG. 4, the loop stand (450) has a relatively small size.

FIG. 12 illustrates an elongated delivery configuration of the device as shown in FIG. 11. Similar to other embodiments, the shunt device (400) is collapsed into an elongated configuration. The braided meshes (432) collapse and slide along the proximal loop strand (450) as the proximal retention flange extends axially. The loop stand (450) can further be stretched and configured to be attached to a delivery catheter (not shown).

In various embodiments, at least one of the shunt portion, the distal portion, and the proximal portion expands radially when the device is deployed in vivo. According to one embodiment of the present teachings, the radial expansion of at least one of the shunt portion, the distal portion, and the proximal portion of the device is due to the elastic nature of the material. According to another embodiment of the present teachings, the radial expansion of at least one of the shunt portion, the distal portion, and the proximal portion of the device is due to its pre-set shape memory of the material. According to yet another embodiment of the present teachings, at least one of the shunt portion, the distal portion, and the proximal portion of the device is radially expanded via a balloon, sometimes, manually.

In the embodiments where the device is expanded in vivo via a balloon, the device is generally mounted a balloon catheter and the inflatable balloon is positioned inside the central lumen of the elongated device. For example, while the device is in its elongated delivery profile, the inflatable balloon can be positioned inside at least one of the shunt portion, the distal portion, and the proximal portion. In some embodiments, after the device is delivered to treatment location, the balloon is then inflated and radially expands at least one of the shunt portion, the distal portion, and the proximal portion of the device. Then upon reaching to desired the balloon can then be deflated and retracted out of the device and back into the delivery catheter. According to another embodiment of the present teachings, the inflatable balloon is positioned inside the central lumen of the entire elongated device. In some embodiments, the device is expanded by inflating the balloon.

According to various embodiments of the present teachings, one or more radioopaque markers are used. Without attempting to limit to any particular function, these radioopaque markers can be visualized by using radiographic imaging equipments such as X-ray, magnetic resonance, ultrasound or other imaging techniques. Marker as disclosed herein can be applied to any part of a device or a delivery system of the present teachings. A radioopaque marker can be weld, sewed, adhered, swaged riveted, otherwise placed, and secured in or on the device. The radioopaque marker may be made of tantalum, tungsten, platinum, irridium, gold, or alloys of these materials or other materials that are known to those skilled in the art. The radioopaque marker can also be made of numerous paramagnetic materials, including one or more elements with atomic numbers 21-29, 42, 44, and 58-70, such as chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III), or other MR visible materials that are known to those skilled in the arts.

In various embodiments, a device of the present teachings includes a flow control element. In some embodiments, the flow control element is a tissue valve. In certain embodiments, the flow control element is as a tricuspid valve, a bicuspid valve, or a single flap valve. In particular embodiments, the flow control element is a ball valve, a duckbill valve, a leaflet valve, a flap valve, a disc in cage type valve, a ball in cage type valve, or other type of valve known to those skilled in the field. In some embodiments, the tissue valve is formed from a bio material or a biocompatible synthetic material. In certain embodiments, the biomaterial is pericardial tissues. In particular embodiments, the pericardial tissues are of the origin of bovine, porcine, ovine or other animal. In certain embodiments, the biocompatible synthetic material is Dacron, Teflon, polyurethane, PET, or other suitable polymer. One skilled in the art would understand that besides the materials discussed herein, a flow control element of the present teachings can be made of any suitable material known in the art.

In some embodiments, the tissue valve is incorporated inside the axial lumen of at least one of the shunt portion, the distal retention flange, and the proximal retention flange of the device. Yet in some other embodiments, the tissue valve is incorporated inside the axial lumen of at least two of the shunt portion, the distal retention flange, and the proximal retention portion of the device. In certain embodiments, the tissue valve is incorporated in the shunt portion and the distal retention flange of the device. In certain embodiments, the tissue valve is incorporated in the shunt portion and proximal retention portion of the device. In yet some other embodiments, the tissue valve is incorporated inside the axial lumen of the entire length of the device. According to some embodiments, the tissue valve is configured to open when the pressure differential reaches a selected value. In some embodiments, the tissue valve remains closed until the pressure differential reaches a selected value.

According to some embodiments, various portions of the device is configured to have different stiffness/flexibility. For example, the distal and proximal retention flanges can be configured to have lesser stiffness than the shunt potion. This way, in many embodiments, inadvertent damages to the septal wall is avoided. In other embodiments, a shunt portion with a relatively great stiffness holds the tissue around the aperture open. In some embodiments, the portion of the retention flanges that contacts the septal tissue is less stiff than another portion of the retention flanges. One skilled in the art would understand that lesser stiffness generally relates greater flexibility and greater stiffness relates lesser flexibility. One skilled in the art would also understand and be capable of constructing various portions of the device with varying stiffness/flexibility so that desired properties for the device can be achieved.

In some embodiments, the stiffness/flexibility for various portions of the device is controlled by the choice of a material. In some embodiments, the stiffness/flexibility for various portions of the device is adjusted by to chemical treatment, a physical treatment, or both. In some embodiments, the stiffness/flexibility of various portions of the device is achieved by ways in which each of the various portions is constructed.

FIG. 13 depicts an embodiment of a device of the present teachings deployed across the atrial septum (2). This device can be that shown in FIGS. 1 and 2. In FIG. 13, the distal retention flange (21) of the device (10) is disposed against the left atrial side of the septal tissue and the proximal retention flange (31) of the device (10) is disposed against the right atrial side of the septal tissue. The shunt portion (40) of the device (10) is positioned through the aperture of the septum (2). The shunt portion (40) of the device in FIG. 13 forms a liquid passageway.

FIGS. 14a-14e illustrate exemplary steps for the deployment of an exemplary device (10) inside a heart according to some embodiments of the present teachings. Once again, the device can be one that is illustrated in FIGS. 1 and 2. According to some embodiments, an aperture is located before the exemplary device (10) is introduced into the treatment site. In the event where no aperture exists in the septum (2), one can be created, for example, by puncturing the septum. Septal puncture procedures are well known to those with ordinary skills in the art. According to some embodiments, after an aperture is created, a guide wire (not shown) is placed across the aperture. In some embodiments, the guide wire is used to guide the delivery and deployment of a device of the present teachings. Alternatively, a delivery assembly can be used to deliver and deploy a device without the need of a guidewire.

In some embodiments, the delivery system (500) is inserted percutaneously by a clinician at an insertion point.

Figure 14A:
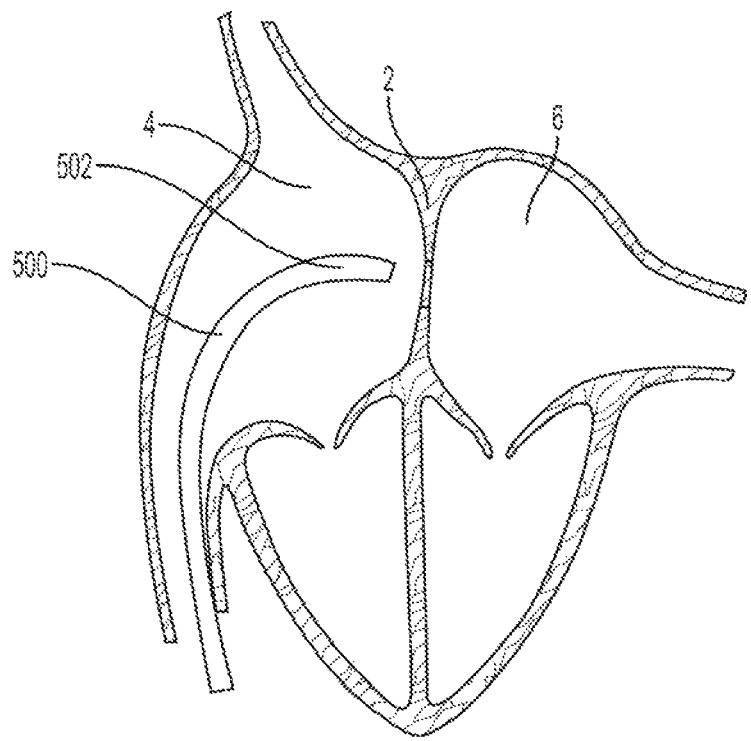

As depicted in FIG. 14*a*, the distal portion (502) of the delivery system (500) is advanced percutaneously into the heart and toward the atrial septum (2). In some embodiments, the delivery system (500) is advanced into the atrial septum (2) through a standard right heart catheterization procedure. In such a procedure, a cardiac implant is delivered through the femoral vein, the inferior vena cava, and the right atrium (4).

In some embodiments, a device, such as the one as shown in FIGS. 1-2, is slidably disposed over a delivery catheter. The axial motion of the device is controlled by the axial motion of the distal portion of the delivery catheter, which in turn is controlled by a clinician outside of the body. In some embodiments, for example, for the device as shown in FIGS. 8, the distal end of a delivery catheter engages the proximal hub or proximal strut(s) of the device during delivery. The axial motion of the device is controlled by the axial motion of the distal portion of the catheter, which in turn is controlled by a clinician outside of the body. In some embodiments, a delivery sheath slides over the delivery catheter and the elongated device to maintain the device in its elongated delivery profile.

In various embodiments, a distal end of the delivery system (500), holding the device (10) in its elongated delivery profile (now shown), extends cross the aperture in the septum (2) and enters the left atrium (6). In some embodiments, a radio-opaque marker is used on the delivery sheath, the delivery catheter, or the device to aid a clinician to determine how far the distal portion of the delivery assembly extends inside the left atrium. According to some embodiments, the device (100) is pre-loaded within the distal end portion (502) of the delivery system (500) and is carried across the atrial septum (2) as the delivery system (500) extends percutaneously. According to other embodiments, the delivery system (500) is positioned across the septum (2) first and then the device (10) is pushed from the proximal end (not shown) to the distal end portion (502) of the delivery system (500).

Figure 14B:
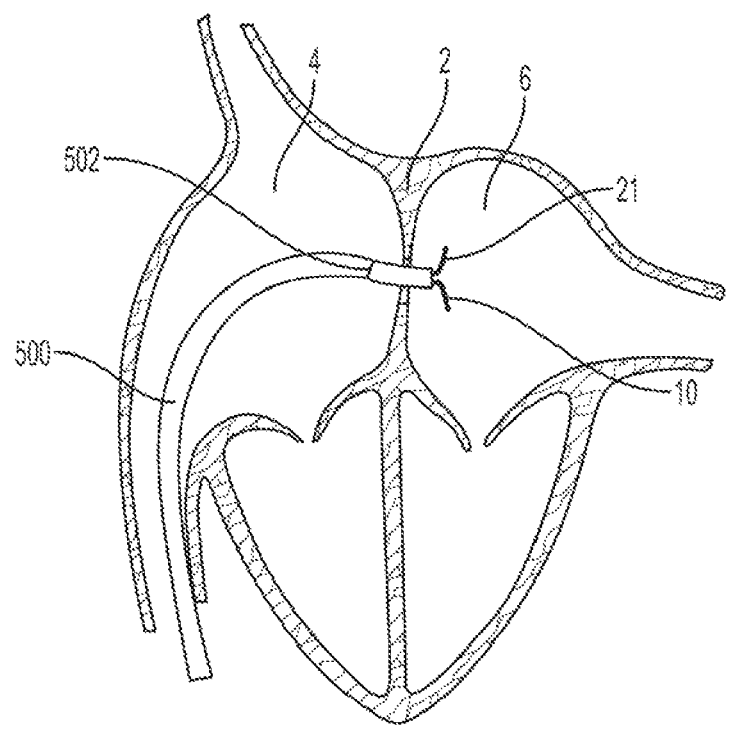

If the clinician is satisfied with the location, the clinician can start to deploy the device (10). In some embodiments, the clinician deploys the distal portion (20) of the device (10) inside the left atrium (6), as shown in FIG. 14*b*. In some embodiments, the delivery system (500) is retracted proximally to expose the distal portion (20) of the device (10). Alternatively, in some embodiments, the device (10) is deployed by pushing the distal portion (20) the device (10) distally out of the distal end portion (502) of the delivery system (500). As the distal portion (20) of the device 10) is exposed outside of the delivery system (500), the distal portion (20) of the device (10) expands radially and contracts axially to resume its pre-set deployed configuration and form. a distal retention flange (21).

Figure 14C:
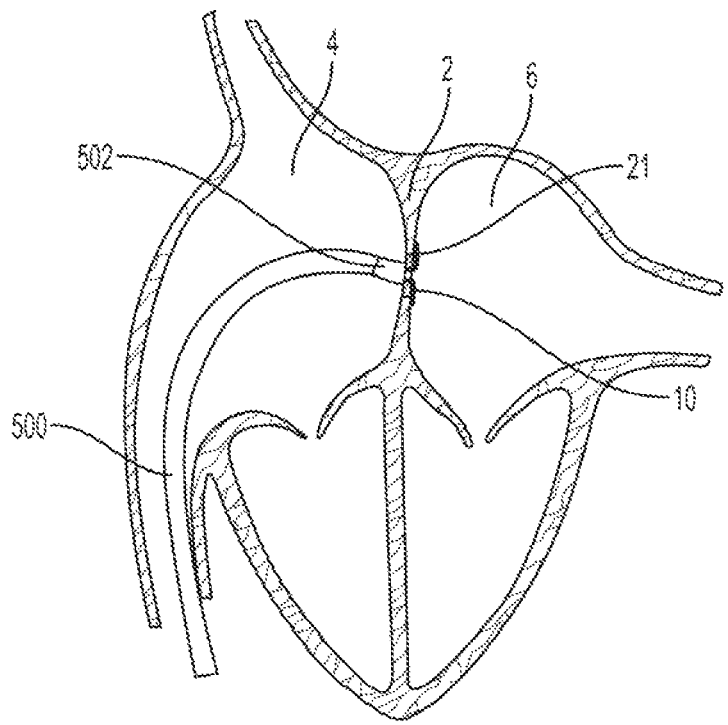

Referring to FIG. 14*c,* the entire delivery assembly (500), including the device (10) with its distal portion (20) deployed outside of the delivery system (500) and its proximal portion (30) still remaining inside the delivery system (500), is retracted proximally. As illustrated in FIG. 14*c,* in some embodiments, the distal retention flange (21) of the device (10) is positioned against the left atrial side of the septum (2). In some other embodiments, the distal retention flange (21) of the device (10) is pulled against the left atrial side of the septum (2).

Figure 14D:
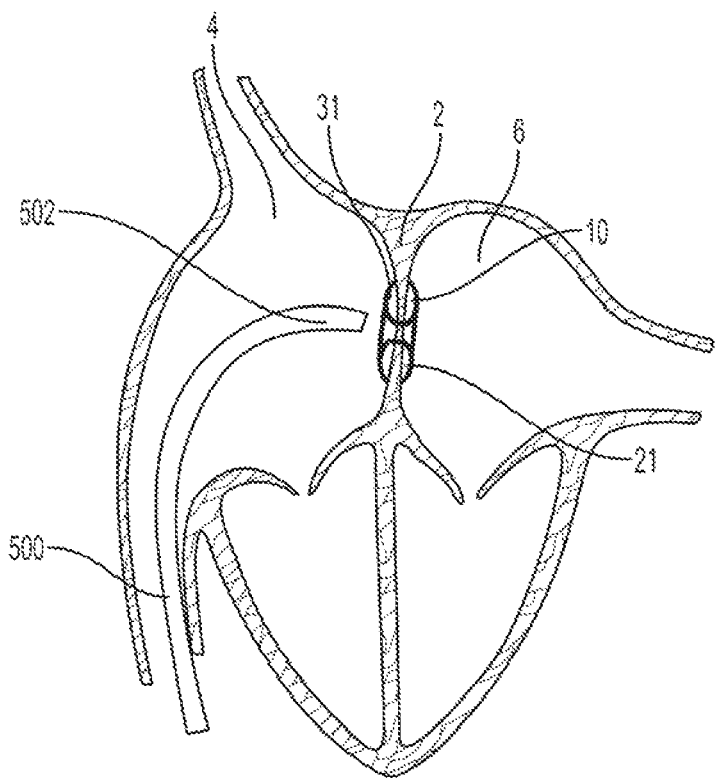

FIG. 14*d* illustrates the deployment of the proximal portion (30) of an exemplary device (10) using similar steps as described herein. According to one embodiment, upon securing the distal retention flange (21) of the device against the left atrial side of the septum (2), the delivery system (500) is withdrawn proximally to expose the proximal portion (30) of the device (10) inside the right atrium (4). As the proximal portion (30) oldie device (10) is exposed, the proximal portion (30) of the device (10) expands radially and contracts axially to resume its pre-set deployed configuration. In certain embodiments, the proximal portion (30) forms a proximal retention flange (31).

Figure 14E:
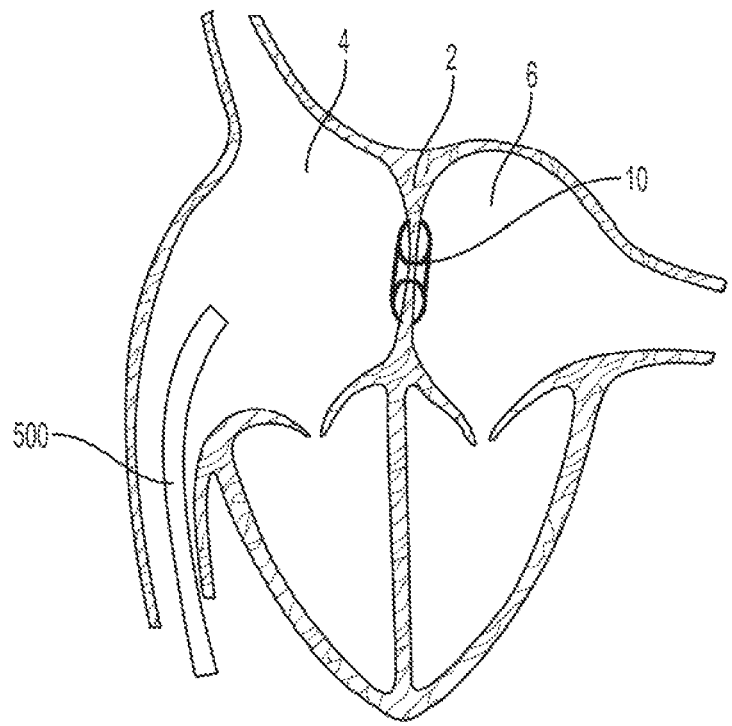

According to one embodiment of the present teachings, for example for the device (10) shown in FIGS. 1-2, after the proximal retention flange (31) is fully deployed, the device (10) is free from the constraint of the delivery system (500). Accordingly, the delivery system (500) can then be removed from the body, as shown in FIG. 14*e*.

In various embodiments, for example, for the device (200) shown in FIGS. 8 and 9, upcoming forming the distal (221) and proximal flanges (231), the proximal end of the device (200) remains engaged with the distal end (502) of the delivery system (500), as shown in FIG. 15. At this point, a clinician can assess the deployment of the device at the treatment location. In some embodiments, the engagement between the proximal end of the device (200) and the distal end (502) of the delivery system (500) can be articulated or pivoted in order to position or adjust the position of the device (200) prior to releasing. These articulable or pivotable engagements are known to those skilled in the art.

Figure 16A:
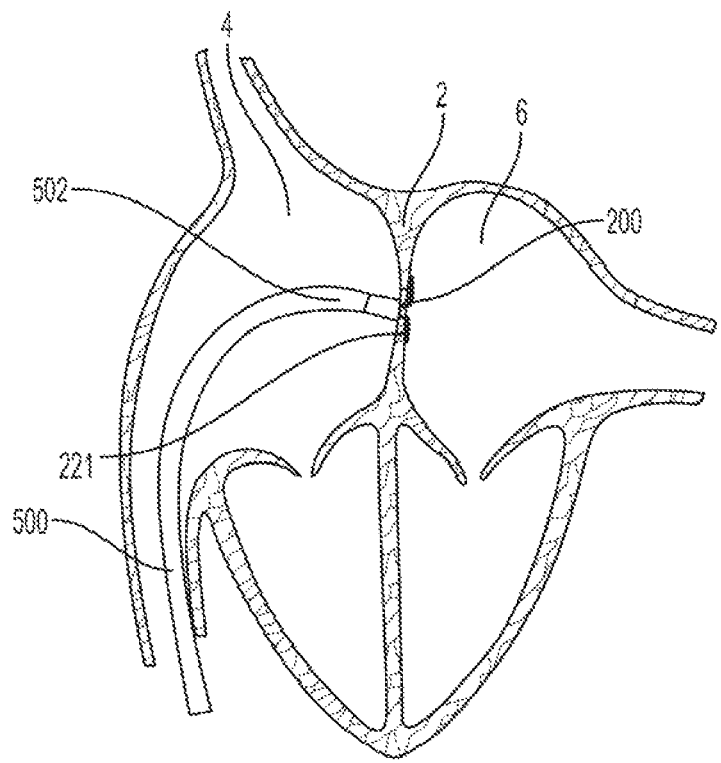
Figure 16B:
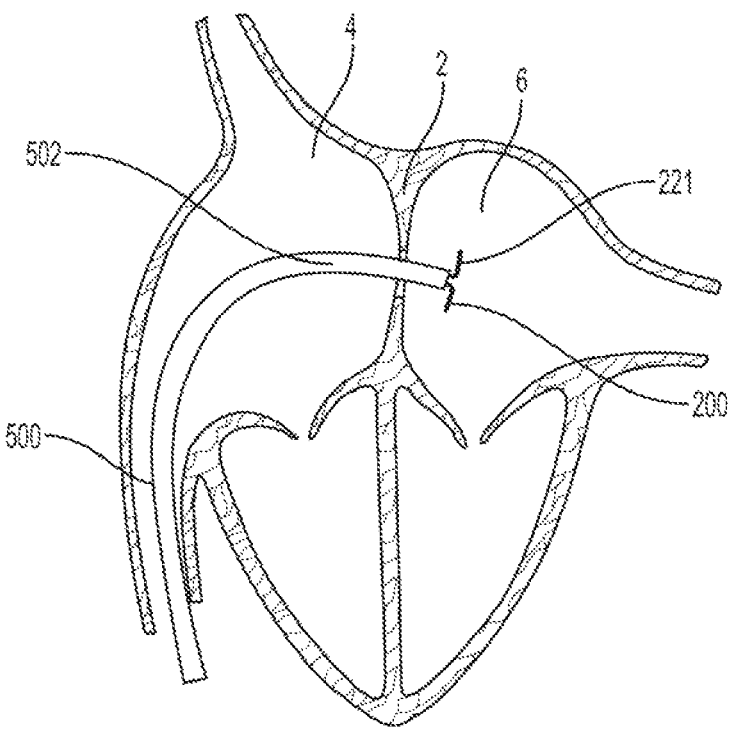
Figure 16C:
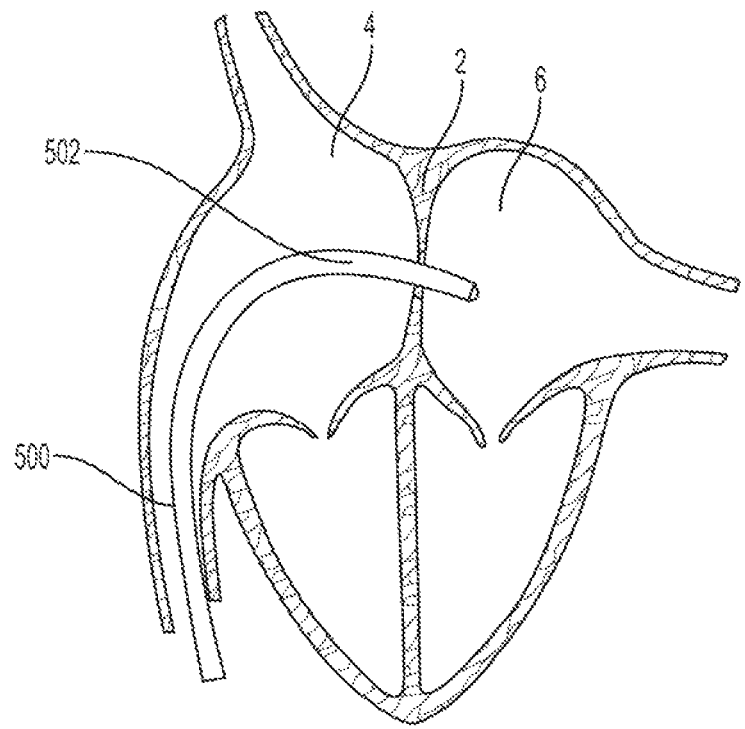

If the clinician is not satisfied with the deployment, the device (200) can be retrieved. During a retrieval, as the proximal end of the device (200) remains engaged to the distal end (502) of the delivery system (500), a clinician pulls the proximal hub (260) of the device (200). At the same time, the delivery system (500) is extended distally. As a result, the distal end portion (502) of the delivery system (500) slides over the proximal portion (230) of the device (200). After the proximal retention flange (231) is fully collapsed, the entire proximal portion (230) of the device (200) enters the distal end portion (502) of the delivery system (500), as shown in FIG. 16*a*. The entire delivery assembly (500) including the device (200) can then extend distally into the left atrium (6), as shown in FIG. 16*b*. A clinician further pulls the proximal hub (260) of the device (200) proximally to collapse the distal retention flange (221). The distal portion (220) of the device (200) slides into the lumen of the distal end portion (502) of the delivery system (500), as shown in FIG. 16*c*. At this point, the entire delivery assembly (500) can be retracted proximally and removed from the patient. Alternatively, the device (200) can be redeployed, by following the steps described herein. Similarly, upon completing a deployment the device (200) at a treatment location, if the clinician is satisfied with the deployment, the device (200) can then be completely released from the delivery system (500). The delivery system (500) can then he withdrawn proximally out of the body.

FIGS. 17-19 illustrate another embodiment of the present teachings. FIG. 17 illustrates an elongated delivery configuration of a device (600) and FIG. 18 illustrates a deployed configuration of the device (600). FIG. 19*a-b* illustrate a perspective views of the device (600) in its deployed configuration. Similar to various embodiments disclosed and discussed herein, the device (600) in these figures is also made from braiding wire(s) or strand(s) of wires with various braiding angels. According to some embodiments, the device (600) includes a proximal and distal retention flanges (631, 621) on each side of a shunt portion (640). Similar to embodiments disclosed herein, the shunt portion (640) has a greater braiding angle than the distal retention flange (621) or/and the proximal retention flange (631). This way, the shunt portion (640) is stiffer than the distal retention flange (621) or/and the proximal retention flange (631). In particularly embodiments, the shunt portion (640) is stiffer axially. As the device (600) is deployed in situ, the relatively stiffer shunt portion (640) prevents the device (600) from collapsing on its own. In some embodiments, a relatively stiff shunt portion (640) (for example, having greater braiding angles or greater braid strand densities than the distal retention flange (621) or the proximal retention flange (631)) reduce ingrowth of surrounding tissues. Similar to the embodiments disclosed in FIG. 10, the proximal ends of the braiding wires are secured to a proximal hub which is configured to attach the device to a delivery system. In some embodiments, when device (600) is deployed, the distal portion (620) of the device expands radially and folds approximately along the midline so that the ends of the distal portion get close to each other and the midline of the distal portion forms a radially outward edge (623). In various embodiments, the distal ends of the braided wires are secured together to form a proximal end of the device. In some embodiments, as the device is being deployed, the proximal portion (630) of the device expands radially and folds approximately at the midline so that the ends of the proximal portion get close to each other and the midline of the proximal portion forms a radially outward edge (633). The shunt portion (640) of the device also expands radially and shortens longitudinally.

According to some embodiments, in order to allow blood to flow through a deployed device, the braiding wire is configured in such way so that upon deployment at least one opening (670), or hole (670), is formed in at least one of the distal and/or proximal retention flanges. FIGS. 19a-b illustrate two exemplary shapes of the openings (670) formed by braiding wires in the proximal retention flange (631). In various embodiments, the distal retention flange includes at least one opening (670). In some embodiments, both the proximal retention flange and the distal retention flange include at least one opening (670). In certain embodiments, the proximal retention flange includes one, two, three, four, five, six, or more openings (670). In certain embodiments, the distal retention flange includes one, two, three, four, five, six, or more openings (670). One skilled in the art would understand that any shape and any number can be used as long as the purpose of allowing blood to flow through a deployed device is served.

Thus, after a device is deployed at a treatment site, the distal flange (621) is positioned against the left atrial side of the septum, the proximal flange (631) is positioned against the right atrial side of the septum, and the shunt portion (640) is positioned across an aperture in the septum. As the left atrial pressure elevates, particularly over a certain value over the right atrial pressure, blood flows from the left atrium through the at least one opening (670) in the distal flange, the shunt portion, and the at least one opening (670) in the proximal flange to reach the right atrium.

FIGS. 17-24 also illustrate another aspect of the present teachings. In various embodiments, a braided shunt device (670) includes an axial constraining, mechanism (680). In various embodiments, the axial constraining mechanism (680) provides additional stiffness to a device (600) of the present teachings. FIG. 18 illustrates one exemplary device. Specifically, in various embodiments, a deployed braided shunt device (600) has radially expanded, generally disc shaped proximal and distal retention flanges (631, 621) at either side of the shunt portion (640). An axial constraining mechanism (680), for example, an axial constraining wire (682) as illustrated in FIG. 18, restrains the axial length of the shunt portion (640) of a deployed device (600). As a result, the stiffness of the shunt portion (640) increases.

According to some embodiments, the axial constraining wire (682) has a distal end (684) connected to the device (600). In some embodiments, a proximal end of the axial constraining wire (682) includes a locking feature (686). In some embodiments, the locking feature is configured to engage a lock receiver (688) on the device. As illustrated in FIG. 18, the distal end (684) of an axial constraining, wire (682) is connected to a place at or near the distal end of the device (600). Alternatively, as illustrated in FIGS. 21-23, the distal end (684) of the axial constraining wire (682) is fixed to a place at or near the distal end of the shunt portion (640) or the proximal retention flange (631) of the device. One skilled in the art would understand that the distal end (684) of the axial constraining wire (682) can be fixed to a place along the longitudinal body of the shunt portion of the device.

In some embodiments, as illustrated in FIGS. 18 and 19, the axial constraint wire (682) includes a locking feature (686). In some embodiments, the locking feature (686) engages a lock receiver (688) at the proximal hub (not shown) of a deployed device. FIG. 21 illustrates another embodiment where the locking feature (686) of the axial constraining wire (682) engages a lock receiver (688) at a place on the proximal retention flange (631). In certain embodiments, the locking feature (686) of the axial constraining wire (682) engages a strand loop (not shown) at or near the proximal end of the proximal retention flange (631). According to another embodiment, as illustrated in FIG. 23, the locking feature (686) of the axial constraining wire (682) engages a lock receiver (688) at a place at or near the proximal end of the shunt portion (640) of a device (600).

According to various embodiments, a lock receiver (688) of the device is configured to engage the locking feature (686) of an axial constraining wire (682). During the deployment of a device (600), the locking feature (686) of the axial constraining wire (682) enters into a distal end of a lock receiver (688). The lock receiver (688) is configured to prevent the locking feature (686) from retracting.

According to some embodiments, the axial constraining wire has a locking feature (686), for example, a ball, and the locking feature is configured to engage a sleeve-like lock receiver (688). Once engaged, the lock receiver (688) prevents the axial constraining wire (682) from being released from the sleeve. An example of a locking feature (686) on an axial constraining wire (682) and a lock receiver (688) is illustrated in FIG. 24. One skilled in the art would understand that many suitable lock designs can be incorporated herein to secure the constraining wire upon deployment of a device. Examples such as wire-crimp securement mechanism, thread securement mechanism, etc. can all be incorporated herein.

As described in details herein, an axial constraining mechanism (680) can include an axial constraining wire (682). While the description herein refers to wires, wires, cables, sutures, or threads are essentially interchangeable. In addition, in some embodiments, each wire, cable, suture, or thread comprises one or more wires, cables, sutures, or threads. According to certain embodiments of the present teachings, the axial constraining wire (682) is made of a variety of materials, including a metal, an alloy (e.g., stainless steel or Nitinol), or a plastic.

FIGS. 17, 20, and 22 illustrate the elongated delivery configurations of devices (600) of the present teachings. In addition, they are shown to be attached to as delivery system (690). In various embodiment, a device (600) of the present teachings is elongated into a tubular profile and an axial constraining wire (682) is not engaged to a lock receiver (688) on the device (600). The axial constraining wire (682) is housed inside the longitudinal body lumen of the elongated device (600). As shown in FIGS. 17, 20, and 22, the proximal end (614) of the device (600) is operably attached to the distal end (694) of a delivery catheter (690). In addition, the proximal end of the axial constraining wire (682) is also operably attached to as distal end (694) of a delivery cable (not shown). In some embodiments, the delivery cable (not shown) is slidably disposed within the axial lumen of the delivery catheter (690). In some embodiments, the delivery cable (not shown) and delivery catheter (690) move independently. According to some embodiments, the device (600) is deployed at a treatment site, similar to the process described herein, in relation to FIGS. 14-16. During the percutaneous deployment process, the axial constraining wire (682) remains attached to the delivery cable (not shown). In some embodiments, the deployment of the device (600) is facilitated with the proximal pulling of the axial constraining wire (682). In some embodiments, the deployment of the device (600) is independent of the movement of the axial constraining wire (682). In some embodiments, the process of locking the axial constraining wire (682) by a lock receiver (688) involves holding the device (600) while pulling the proximal end of the axial constraining wire (682) proximally and engaging the locking feature (686) with the lock receiver (688) of the device (600). In some embodiments, the engagement of the axial constraining wire (682) is the last step of a device deployment. In some embodiments, the engagement of the axial constraining wire (682) is before the last step of a device deployment. Upon a satisfactory deployment, the axial constraining wire (682) disengages from the delivery cable (not shown). In some embodiments, for example, where the axial constraining mechanism (680) is made of suture (682) and the lock receiver (688) on the device is a crimp mechanism, after the axial constraining wire (682) is engaged with the lock receiver (688) via the locking feature (686), any excess suture could be cut and removed from the body.

The techniques disclosed for deploying the embodiments described herein are solely for illustration. One skilled in the art should understand that specific steps for deployment, retrieval varies according to the detail configuration of the device. It should be understood that other techniques can be used instead of, or in combination with, these disclosure, especially because a clinician can select a technique to deploy an embodiment of the devices described herein based on the particular features of the device, the delivery system, and the anatomy in which the device is being deployed. Thus, the exemplary deployment and retrieval method described here should not be viewed as limiting to the scope of the present teaching.

The methods and devices disclosed above are useful for treating various symptoms of heart failures, in particular, diastolic heart failures, by reducing the pressure in the left atrium and pulmonary veins. One skilled in the art would recognize that devices according to the present teachings can be used to regulate pressure in other parts of the heart and/or vascular portions of the body. For example, the devices disclosed herein can be deployed on the septum between the left and right atria, the left and right ventricles, left atrium and coronary sinuses, and the like.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can he used in the practice or testing of the present teachings. In case of conflict, the patent specification, including definitions, will control. In addition, the materials, methods, and examples are illustrative only and not intended to be limiting.

I claim:

1. An implantable medical device comprising a braided structure, wherein the braided structure is unitary in construction, a shunt portion comprising a distal end, proximal end, and a tubular body, a distal retention flange comprising a free end and a fixed end, wherein in a deployed profile of the implantable medical device, the fixed end of the distal retention flange connects to the distal end of the shunt portion and the free end of the distal retention flange extends radially outwardly from the fixed end of the distal retention flange and is the most radially outward portion of the distal retention flange, a proximal retention flange comprising a free end and a fixed end, wherein the fixed end of the proximal retention flange connects to the proximal end of the shunt portion, and the free end of the proximal retention flange extends radially outwardly from the fixed end of the proximal retention flange, the distal and proximal retention flanges comprising a diameter of at least 1.2 times that of the shunt portion, and wherein the shunt portion comprises a diameter of about 5-30 mm, and wherein the implantable medical device also comprises a delivery profile in which the shunt portion comprises a first braid angle, the distal retention flange comprises a second braid angle, and the proximal retention flange comprises a third braid angle, wherein the first braid angle is greater than the second and third braid angles, wherein the shunt portion is configured to be positioned within an aperture in an atrial septum, and wherein the shunt portion comprises a hoop strength sufficient to keep the aperture open and allow blood flow from the left atrium to reduce elevated pressure.

2. The implantable medical device of claim 1, wherein the shunt portion has first hoop stiffness, the distal retention flange has a second hoop stiffness, and the proximal retention flange has a third hoop stiffness, wherein the first hoop stiffness is greater than at least one of the second hoop stiffness and third hoop stiffness.

3. The implantable medical device of claim 1, wherein the free end of the proximal retention flange connects to a proximal hub.

4. The implantable medical device of claim 1, wherein the shunt portion comprises a first diameter and a braid angle $\theta$, the distal retention flange comprises a second diameter, and the proximal retention flange comprises a third diameter, wherein the ratio of the second or third diameter to the first diameter equals or is greater than $1/\sin \theta$.

5. The implantable medical device of claim 1, comprising a constraint, wherein the constraint comprises a locking feature and a lock receiver.

6. The implantable medical device of claim 5, wherein the constraint comprises an axial constraining wire, wherein the axial constraining wire is attached to the distal retention flange and the locking feature is located at a proximal end of the axial constraining wire.

7. The implantable medical device of claim 5, wherein the constraint comprises an axial constraining wire, wherein the axial constraining wire is attached to the shunt portion and the locking feature is located at a proximal end of the axial constraining wire.

8. The implantable medical device of claim 5, wherein the locking feature comprises a ball.

9. The implantable medical device of claim 5, wherein the lock receiver is attached to the medical device.

10. The implantable medical device of claim 5, wherein the lock receiver is attached to the proximal retention flange.

11. The implantable medical device of claim 5, wherein the lock receiver is attached to the shunt portion.

12. The implantable medical device of claim 5, wherein the lock receiver is attached to the distal retention flange.

13. The implantable medical device of claim 1, wherein the distal retention flange comprises an inner tubular surface when the implantable medical device is at its delivery profile, wherein the inner tubular surface transitions to form a surface facing away from the shunt portion when the implantable medical device transitions from its delivery profile to its deployed profile.

14. The implantable medical device of claim 1, wherein the proximal retention flange comprises an inner tubular surface when the implantable medical device is at its delivery profile, wherein the inner tubular surface transitions to form a surface facing away from the shunt portion when the implantable medical device transitions from its delivery profile to its deployed profile.

15. The implantable medical device of claim 1, wherein the free end of the distal retention flange transitions radially outwardly to form the radially outward edge of a generally disc-like distal retention flange when the implantable medical device transitions from its delivery profile to its deployed profile.

16. The implantable medical device of claim 1, wherein the free end of the proximal retention flange transitions radially outwardly to form the radially outward edge of a generally disc-like proximal retention flange when the implantable medical device transitions from its delivery profile to its deployed profile.

17. A method of treating heart failure with an implantable medical device, wherein the implantable medical device comprises a braided structure, wherein the braided structure is unitary in construction; wherein the implantable medical device comprises a shunt portion comprising a distal end, a proximal end, and a tubular body, a distal retention flange comprising a free end, a fixed end, and an inner tubular surface, wherein the fixed end of the distal retention flange connects to the distal end of the shunt portion, and a proximal retention flange comprising a free end and a fixed end, wherein the fixed end of the proximal retention flange connects to the proximal end of the shunt portion, and wherein the shunt portion comprises a first braid angle, the distal retention flange comprises a second braid angle, and the proximal retention flange comprises a third braid angle, wherein the first braid angle is greater than the second and third braid angles, and wherein the shunt portion is configured to be positioned in an aperture in an atrial septum of a patient and comprising a hoop strength sufficient to keep the aperture open and allow blood flow from the left atrium to reduce elevated pressure, and wherein the distal and proximal retention flanges comprise a diameter of at least 1.2 times that of the shunt portion, and wherein the shunt portion comprises a diameter of about 5-30 mm; and wherein the implantable medical device comprises a delivery profile and a deployed profile; the method comprising advancing the distal retention flange of the implantable medical device at its delivery profile through the atrial septum into the left atrium in which the free end of the distal retention flange is the distal most portion of the implantable medical device, and transitioning the free end of the distal retention flange to a generally disc-like shape wherein the free end of the distal retention flange extends radially outwardly from the fixed end of the distal retention flange and is the most radially outward portion of the distal retention flange and the inner tubular surface transitions to form a surface facing away from the shunt portion.

18. The method of claim 17, comprising transitioning the free end of the proximal retention flange to a generally disc-shape wherein the free end of the proximal retention flange extends radially outwardly from the fixed end of the proximal retention flange and the inner tubular surface of the proximal retention flange transitions to form a surface facing away from the shunt portion.

19. A device comprising an implantable medical device and a catheter, wherein the catheter comprises a distal end, a proximal end, and a lumen extends proximally from the distal end; the implantable medical device comprises a braided structure, wherein the braided structure is unitary in construction, a shunt portion configured to be positioned in an aperture in an atrial septum of a patient and comprising a hoop strength sufficient to keep the aperture open and allow blood flow from the left atrium to reduce elevated pressure, the shunt portion comprising a distal end, a proximal end, and a tubular body, a distal retention flange comprising a free end and a fixed end, wherein in a deployed profile of the implantable medical device, the fixed end of the distal retention flange connects to the distal end of the shunt portion and the free end of the distal retention flange extends radially outwardly from the fixed end of the distal retention flange and is the most radially outward portion of the distal retention flange, a proximal retention flange comprising a free end and a fixed end, wherein the fixed end of the proximal retention flange connects to the proximal end of the shunt portion, wherein the distal and proximal retention flanges comprise a diameter of at least 1.2 times that of the shunt portion, and wherein the shunt portion comprises a diameter of about 5-30 mm, and wherein implantable medical device comprises a delivery profile in which the shunt portion comprises a first braid angle, the distal retention flange comprises a second braid angle, and the proximal retention flange comprises a third braid angle, wherein the first braid angle is greater than the second and third braid angles.

* * * * *